US011819305B1

(12) United States Patent
Volkerink et al.

(10) Patent No.: US 11,819,305 B1
(45) Date of Patent: Nov. 21, 2023

(54) METHOD FOR DETERMINING DIRECTION OF MOVEMENT THROUGH GATES AND SYSTEM THEREOF

(71) Applicant: Trackonomy Systems, Inc., San Jose, CA (US)

(72) Inventors: Hendrik J Volkerink, Palo Alto, CA (US); Ajay Khoche, West San Jose, CA (US)

(*) Notice: Subject to any disclaimer, the term of this patent is extended or adjusted under 35 U.S.C. 154(b) by 0 days.

(21) Appl. No.: 17/494,510

(22) Filed: Oct. 5, 2021

Related U.S. Application Data

(60) Provisional application No. 63/123,451, filed on Dec. 9, 2020, provisional application No. 63/087,304, filed on Oct. 5, 2020.

(51) Int. Cl.
*H04W 4/029* (2018.01)
*A61B 5/00* (2006.01)
*B32B 27/36* (2006.01)
*G06K 7/00* (2006.01)

(52) U.S. Cl.
CPC ............ *A61B 5/0002* (2013.01); *B32B 27/36* (2013.01); *G06K 7/00* (2013.01); *H04W 4/029* (2018.02); *B32B 2307/546* (2013.01)

(58) Field of Classification Search
CPC ....... H04W 4/029; H04W 4/38; H04W 4/026; H04W 4/027; G06K 7/00; G06N 20/00
See application file for complete search history.

(56) References Cited

U.S. PATENT DOCUMENTS

| 5,495,250 | A | | 2/1996 | Ghaem et al. |
| 5,528,232 | A | * | 6/1996 | Verma ............... G06K 7/10346 340/8.1 |
| 5,714,932 | A | * | 2/1998 | Castellon .......... G08B 21/0263 455/67.11 |
| 6,404,341 | B1 | | 6/2002 | Reid |
| 6,499,025 | B1 | | 12/2002 | Horvitz et al. |
| 6,502,033 | B1 | | 12/2002 | Phuyal |

(Continued)

FOREIGN PATENT DOCUMENTS

| AU | 2018204317 A1 | 1/2019 |
| AU | 2018250358 A1 | 5/2019 |

(Continued)

OTHER PUBLICATIONS

Dementyev, SensorTape: Modular and Programmable 3D-Aware Dense Sensor Network on a Tape, In Proc. of UIST 2015.

(Continued)

*Primary Examiner* — Daniel I Walsh

(57) ABSTRACT

A method for tracking assets in areas of interest includes receiving, by a first node of a wireless sensing system, a first communication and a second communication by a tape node associated with a mobile asset and receiving, by a second node of the wireless sensing system, the first communication and the second communication by the tape node associated with the mobile asset. A direction of movement of the tape node associated with the mobile asset is computed, the direction of movement based at least in part on respective signal strengths of the first communication and the second communication as received by the first node and the second node. Based on the direction of movement, a most likely path of the tape node is determined.

20 Claims, 14 Drawing Sheets

(56) References Cited

U.S. PATENT DOCUMENTS

| | | | |
|---|---|---|---|
| 6,502,082 B1 | 12/2002 | Toyama et al. | |
| 7,048,194 B2 | 5/2006 | Minami et al. | |
| 7,177,054 B2 | 2/2007 | Silverbrook et al. | |
| 7,299,990 B2 | 11/2007 | Hoshina | |
| 7,405,656 B2 | 7/2008 | Olsen | |
| 7,540,603 B2 | 6/2009 | Otsuki | |
| 7,646,336 B2 | 1/2010 | Tan et al. | |
| 7,722,249 B2 | 5/2010 | Kim et al. | |
| 7,756,639 B2 | 7/2010 | Colley et al. | |
| 7,838,844 B2 | 11/2010 | Wagner et al. | |
| 7,884,727 B2 | 2/2011 | Tran | |
| 8,072,620 B2 | 12/2011 | Yamamoto et al. | |
| 8,110,254 B1 | 2/2012 | Sharma et al. | |
| 8,292,173 B2 | 10/2012 | Yturralde et al. | |
| 8,751,151 B2 | 6/2014 | Funk et al. | |
| 8,751,162 B1 | 6/2014 | Barbeau et al. | |
| 8,774,830 B2 | 7/2014 | Ziskind et al. | |
| 8,786,510 B2 | 7/2014 | Coleman et al. | |
| 8,833,664 B2 | 9/2014 | Choi | |
| 9,075,141 B2 | 7/2015 | Syed et al. | |
| 9,146,113 B1 | 9/2015 | Funk et al. | |
| 9,534,908 B2 | 1/2017 | Kitchel et al. | |
| 9,664,521 B2 | 5/2017 | Funk et al. | |
| 9,684,081 B2 | 6/2017 | Giurgiu et al. | |
| 9,693,689 B2 | 7/2017 | Gannon et al. | |
| 9,766,344 B2 | 9/2017 | Ichinokawa | |
| 9,766,349 B1 | 9/2017 | Madhow et al. | |
| 10,902,310 B2 | 1/2021 | Khoche | |
| 11,093,810 B1* | 8/2021 | Jones | G06K 19/0728 |
| 11,115,732 B2 | 9/2021 | Lucrecio et al. | |
| 11,356,846 B2* | 6/2022 | Osborn | H04W 4/029 |
| 2002/0024448 A1* | 2/2002 | Olesen | G01S 13/765 |
| | | | 340/8.1 |
| 2002/0193940 A1 | 12/2002 | Hashida | |
| 2003/0163287 A1 | 8/2003 | Vock et al. | |
| 2004/0061605 A1* | 4/2004 | Howard | G01S 17/00 |
| | | | 340/539.11 |
| 2004/0075606 A1 | 4/2004 | Laiho et al. | |
| 2006/0281473 A1 | 12/2006 | Debany et al. | |
| 2007/0010940 A1 | 1/2007 | Tan et al. | |
| 2007/0287473 A1 | 8/2007 | Dupray | |
| 2007/0247316 A1* | 10/2007 | Wildman | G08B 21/0263 |
| | | | 340/572.4 |
| 2008/0055155 A1* | 3/2008 | Hensley | G01S 5/0027 |
| | | | 342/357.34 |
| 2008/0079567 A1 | 4/2008 | Poor | |
| 2008/0082254 A1 | 4/2008 | Huhtala et al. | |
| 2008/0198002 A1 | 8/2008 | Bartholf et al. | |
| 2008/0218354 A1* | 9/2008 | Lorentz | G06K 7/0008 |
| | | | 340/572.1 |
| 2009/0009327 A1 | 1/2009 | Amidi | |
| 2009/0174600 A1 | 7/2009 | Mazlum et al. | |
| 2009/0192709 A1 | 7/2009 | Yonker et al. | |
| 2009/0196267 A1 | 8/2009 | Walker, Sr. | |
| 2009/0280827 A1 | 11/2009 | Michaud | |
| 2009/0326809 A1 | 12/2009 | Colley et al. | |
| 2010/0230498 A1 | 9/2010 | Atherton | |
| 2011/0110242 A1 | 5/2011 | Nixon et al. | |
| 2011/0192465 A1 | 8/2011 | Collings | |
| 2011/0313648 A1 | 12/2011 | Newson et al. | |
| 2012/0271540 A1 | 10/2012 | Miksa et al. | |
| 2012/0278676 A1 | 11/2012 | Teraura | |
| 2013/0099927 A1* | 4/2013 | Kulinets | G08B 13/2462 |
| | | | 340/572.1 |
| 2013/0131980 A1 | 5/2013 | Ginsberg | |
| 2013/0250357 A1 | 9/2013 | Yu | |
| 2013/0332064 A1 | 12/2013 | Funk et al. | |
| 2014/0058661 A1 | 2/2014 | Choi et al. | |
| 2014/0172293 A1 | 6/2014 | Chang et al. | |
| 2014/0306694 A1* | 10/2014 | Oprea | G06K 19/0723 |
| | | | 235/492 |
| 2015/0149073 A1 | 5/2015 | Ishigami et al. | |
| 2015/0153437 A1* | 6/2015 | Baumgartner | G01S 5/0289 |
| | | | 342/452 |
| 2015/0154531 A1 | 6/2015 | Skaaksrud | |
| 2015/0154535 A1* | 6/2015 | Wappler | G06Q 10/087 |
| | | | 705/28 |
| 2015/0230058 A1 | 8/2015 | Cho et al. | |
| 2015/0285636 A1 | 10/2015 | Funk et al. | |
| 2015/0287301 A1* | 10/2015 | Locke | G08B 13/00 |
| | | | 348/156 |
| 2015/0349917 A1* | 12/2015 | Skaaksrud | H04W 4/029 |
| | | | 370/328 |
| 2016/0026213 A1 | 1/2016 | Li et al. | |
| 2016/0109583 A1 | 4/2016 | Willis | |
| 2016/0110085 A1 | 4/2016 | Barton et al. | |
| 2016/0188181 A1 | 6/2016 | Smith | |
| 2016/0205509 A1 | 7/2016 | Hopcraft et al. | |
| 2016/0269533 A1 | 9/2016 | Taylor et al. | |
| 2016/0358444 A1 | 12/2016 | Lundy | |
| 2017/0010363 A1 | 1/2017 | Friend | |
| 2017/0074659 A1 | 3/2017 | Giurgiu et al. | |
| 2017/0089717 A1 | 3/2017 | White et al. | |
| 2017/0173262 A1* | 6/2017 | Veltz | G16H 20/17 |
| 2017/0219351 A1 | 8/2017 | Hamilton et al. | |
| 2017/0337405 A1 | 11/2017 | Schutz | |
| 2017/0347940 A1 | 12/2017 | Carr | |
| 2018/0003507 A1 | 1/2018 | Arslan et al. | |
| 2018/0124646 A1* | 5/2018 | Thubert | H04W 48/18 |
| 2018/0190096 A1 | 7/2018 | Lundy | |
| 2019/0037362 A1 | 1/2019 | Nogueira-Nine | |
| 2019/0079510 A1* | 3/2019 | Ferris | G05D 1/0022 |
| 2019/0149990 A1 | 5/2019 | Wang et al. | |
| 2019/0250653 A1 | 8/2019 | Conlon | |
| 2020/0072485 A1 | 3/2020 | LaPalme | |
| 2020/0100115 A1 | 3/2020 | Skaaksrud | |
| 2020/0229206 A1* | 7/2020 | Badic | H04W 52/0209 |
| 2021/0020012 A1 | 1/2021 | Shakedd | |
| 2021/0165977 A1* | 6/2021 | Cheng | G06K 7/10356 |
| 2021/0271786 A1* | 9/2021 | Duff | G06Q 10/10 |
| 2022/0068142 A1* | 3/2022 | Anderton | H04W 4/40 |
| 2022/0092376 A1* | 3/2022 | Volkerink | G06Q 10/0833 |
| 2022/0100263 A1 | 3/2022 | Nagar et al. | |
| 2022/0110189 A1* | 4/2022 | Volkerink | H04W 4/35 |
| 2022/0120857 A1* | 4/2022 | Moritz | H04B 17/318 |
| 2022/0162013 A1* | 5/2022 | Cheon | B07C 3/00 |
| 2022/0167122 A1* | 5/2022 | Volkerink | G16Y 30/00 |
| 2022/0353648 A1* | 11/2022 | Volkerink | H04W 4/35 |
| 2023/0025103 A1* | 1/2023 | Volkerink | H04W 4/33 |
| 2023/0171575 A1* | 6/2023 | Thubert | H04W 48/18 |
| | | | 370/255 |

FOREIGN PATENT DOCUMENTS

| | | |
|---|---|---|
| CA | 3 061 878 A1 | 11/2018 |
| CA | 3 008 512 A1 | 12/2018 |
| JP | 2008239282 | 10/2008 |
| JP | 2011090670 | 5/2011 |
| JP | 2012141995 | 7/2012 |

OTHER PUBLICATIONS

Pyo et al., Development of a Map Matching Method Using the Multiple Hypothesis Technique, 2001 IEEE.

Liu, Survey of Wireless Based Indoor Localization Technologies, arXiV:1709.01015v2 [cs,NI] Mar. 14, 2018.

Cheung et al., Least Squares Algorithms for Time-of-Arrival-Based Mobile Location, IEEE Transactions on Signal Processing, vol. 52, No. 4, Apr. 2004, pp. 1121-1128.

Frazier et al., Fully-Drawn Carbon-Based Chemical Sensors on Organic and Inorganic Surfaces, Lap Chip. Oct. 21, 2014; 14(20): 4059-4066. doi:10.1039/c4lc00864b.

Alsheikh et al., Machine Learning in Wireless Sensor Networks: Algorithms, Strategies, and Applications, arXiv:1405.4463v2 [cs.NI] Mar. 19, 2015.

Gong et al., Low-Cost Sensor Tape for Environment Sensing Based on Roll-to-Roll Manufacturing Process, In Proc. of IEEE Sensors 2012, 4 pages.

Olyazadeh, Least Square Approach on Indoor Positioning Measurement Techniques, 2012.

(56) References Cited

OTHER PUBLICATIONS

Zhang et al., Deep Neural Networks for Wireless Localization in Indoor and Outdoor Environments, Neurocomputring 194 (2016), pp. 279-287.
A. Celmins, Multidimensional Least-Squares Fitting of Fuzzy Models, Math Modelling, vol. 9. No. 9, pp. 669-690, 1987.
Fischer, "Selecting the length of a principal curve within a Gaussian model," Electronic Journal of Statistics, vol. 7, (2013) 342-363, Jan. 2013.
Krach et al., "Intergration of Foot-Mounted Inertial Sensors into a Bayesian Location Estimation Framework," Proceedings of the 5th Workshop on Positioning, Navigation and Communication 2008 (WPNC'08), pp. 55-61.
C. Fouque et al., "Tightly-coupled GIS data in GNSS fix computations with integrity testing," Int. J. Intelligent Information and Database Systems, vol. 2, No. 2, 2008, pp. 167-186.
Brunsdon, "Path Estimation from GPS Tracks," Department of Geography. University of Leicester. University Road, Leicester LE1 7RU, pp. 1-9, 2007.
Scott, "Improved GPS Positioning for Motor Vehicles Through Map Matching," University of Technology, Sydney, ION-94, Salt Palace Convention Center, Salt Lake City, Utah, Sep. 20-23, 1994.
Einbeck et al. "Exploring multivariate data structures with local principal curves", in Proceedings of the 28th Annual Conference of the Gesellschaft fur Klassikation, Mar. 9-11, 2004, University of Dortmund. Heidelberg: Springer-Verlag, pp. 256-263.
Blewitt et al., "Mapping Dilution of Precision (MDOP) and map-matched GPS," Int. J. Geographical Information Science, 2002, vol. 16, No. 1, 55-67.
Biau et al., "Parameter Selection for Principal Curves" IEEE Transactions on Information Theory, vol. 58, No. 3, Mar. 2012, 16 pages.
Rabe et al, "Lane-level map-matching based on optimization" 2016 IEEE 19th International Conference on Intelligent Transportation Systems (ITSC), Windsor Oceanico Hotel, Rio de Janeiro, Brazil, Nov. 1-4, 2016.
Bierlaire et al., "A method of probabilistic map distribution of path likelihood," STRC 2009, 9th Swiss Transport Research Conference, Sep. 2009, pp. 1-13.
Quddus et al., "Current map-matching algorithms for transport applications: State-of-the art and future research directions," Transportation Research Part C: Emerging Technologies, vol. 15, Issue 5, Oct. 2007, pp. 312-328.
International Search Report and Written Opinion dated Mar. 29, 2019, in International Application No. PCT/US2018/064859, filed Dec. 11, 2018.
International Patent Application No. PCT/US2021/062712 International Search Report and Written Opinion dated May 23, 2022, 10 pages.
U.S. Appl. No. 17/449,934, Notice of Allowance dated Jun. 14, 2022, 10 pages.
U.S. Appl. No. 17/126,796, Office Action dated Mar. 24, 2022, 11 pages.

\* cited by examiner

METHOD FOR DETERMINING DIRECTION OF MOVEMENT THROUGH GATES AND SYSTEM THEREOF

CROSS-REFERENCE TO RELATED APPLICATIONS

This application claims priority to U.S. Provisional Patent Application No. 63/087,304, filed on Oct. 5, 2020, and to U.S. Provisional Patent Application No. 63/123,451, filed on Dec. 9, 2020, each of which is incorporated herein in its entirety.

FIELD OF THE DISCLOSURE

This disclosure generally relates to wireless internet of things (IOT) devices and, more specifically, to asset tracking.

BACKGROUND

In fast-paced environments such as hospitals, assets may be moved frequently throughout buildings, wards, or other sections of an area. It is valuable to track assets as movement occurs in order to ensure that assets are accounted for, e.g., are not lost or misrepresented as being in or out of use. Tracking devices may be used to monitor assets; however, because assets may be moved quickly and unpredictably, there are difficulties in optimizing power usage and accurate data collection of tracking devices for asset tracking.

SUMMARY

In an aspect, a wireless sensing system monitors heartbeat signals to monitor locations and usage information for assets. Heartbeat signals are low-power signals transmitted periodically by nodes of the wireless sensing system associated with assets, e.g., tape nodes adhered or affixed to machines or items. For most applications, heartbeat signals are transmitted infrequently, e.g., once a day, once an hour. However, in fast-paced environments such as hospitals, it is possible for assets to be moved too quickly for heartbeat signals to provide useful information. For example, an asset such as a bed loaded onto an ambulance may be moved too quickly for the wireless sensing system to accurately receive data corresponding to the movement. While increasing the frequency of the heartbeat signals, e.g., a heartbeat per second, may accommodate fast-moving assets, high frequency heartbeats drains battery life of tape nodes.

In an embodiment, a wireless sensing system deploys one or more sets of gateway nodes through a building or area of interest to detect assets moving through gates. Gates may be, for example, doorways, hallways, or other threshold areas. In an embodiment, a direction of movement through a gate may be used by the wireless sensing system to approximate a likely location for the asset. For example, an asset moving through an external loading door of a hospital is tagged by the wireless sensing system as most likely being loaded onto an ambulance. The one or more sets of gateway nodes are configured to receive heartbeat signals from tape nodes associated with assets and to determine, based on the respective signal strengths of the heartbeat signals, a direction of movement for assets. In some embodiments, the one or more sets of gateway nodes are deployed in locations throughout a building or area of interest based on structural thresholds. For example, a first node of a set of gateway nodes is deployed inside of a room and a second node of the set of gateway nodes is deployed in a hallway outside of the room, enabling the wireless sensing system to ensure that an asset is accurately tracked as passing through the door. In some examples, a node of a set of gateway nodes deployed inside of a room is further configured to conduct a check for an asset being within a room to confirm that the asset has moved through a doorway threshold.

In an embodiment, the wireless sensing system trains and applies a machine learned model. The machine learned model is trained to receive as input one or more signals associated with one or more signal strengths and to output a most likely direction of movement for an asset. For example, the machine learned model outputs a label identifying a direction (e.g., north, south, west, east), a name of a corresponding location (e.g., ambulance loading area, storage room, etc.), or the like.

To ensure that a tape node associated with a moving asset transmits heartbeat signals at appropriate intervals to optimize battery life and to provide adequate information for signal strength computations, the wireless sensing system transmits instructions to tape nodes to identify certain contexts or locations in which a higher frequency heartbeat signal is required. Because shorter range communications are more battery-efficient than longer range communications, it is beneficial for tape nodes to communicate heartbeat signals to gateway nodes when in short range. In an embodiment, gateway nodes are deployed as leading indicators through a building or area of interest to provide instructions to tape nodes to increase a heartbeat signal frequency upon approaching a gate. For example, a gateway node is located at an entrance of a loading zone and instructs tape nodes within the loading zone to increase a frequency of heartbeat signal as the tape nodes move towards a threshold door. In another example, one or more gateway nodes are located at conveyer belts and are configured to instruct tape nodes on the conveyer belt to increase a frequency of heartbeat signals within a threshold amount of time (e.g., increase heartbeat signal in 5 minutes).

In other embodiments, the gateway node may provide other or additional instructions to a tape node. For example, the gateway node may additionally instruct a tape node to increase or decrease an amount of sensor data collection, to increase or decrease an amount of data transmittal, to modify a means or channel for communication, to establish or disconnect to another entity of the wireless sensing system, and the like. In another example, the gateway node may instruct a tape node to decrease or reduce a frequency of heartbeat pings or other communications, e.g., at the threshold to a long-term storage room in which it is unlikely to be moved and, as such, can reduce communications to preserve battery life.

A method for determining direction of movement of assets through gates is also disclosed herein. A first node of a wireless sensing system receives a first communication and a second communication by a tape node associated with a mobile asset. The first communication and the second communication are associated with respective signal strengths and respective timestamps. A second node of the wireless sensing system receives a first communication and a second communication by the tape node associated with the mobile asset, associated with respective signal strengths and timestamps. The first and second nodes of the wireless sensing system are associated with location information (e.g., are stationary gateway nodes deployed in a building or area of interest). The wireless sensing system computes a direction of movement of the tape node associated with the mobile asset based at least in part on the respective signal strengths of the first and second communications. Based on the direction of movement, the wireless sensing system determines a most likely path of the tape node.

Embodiments of the subject matter described in this specification include methods, processes, systems, apparatus, and tangible non-transitory carrier media encoded with one or more program instructions for carrying out one or more methods and processes for enabling the various functionalities of the described systems and apparatus.

Other features, aspects, objects, and advantages of the subject matter described in this specification will become apparent from the description, the drawings, and the claims.

DETAILED DESCRIPTION

Figure 1A:
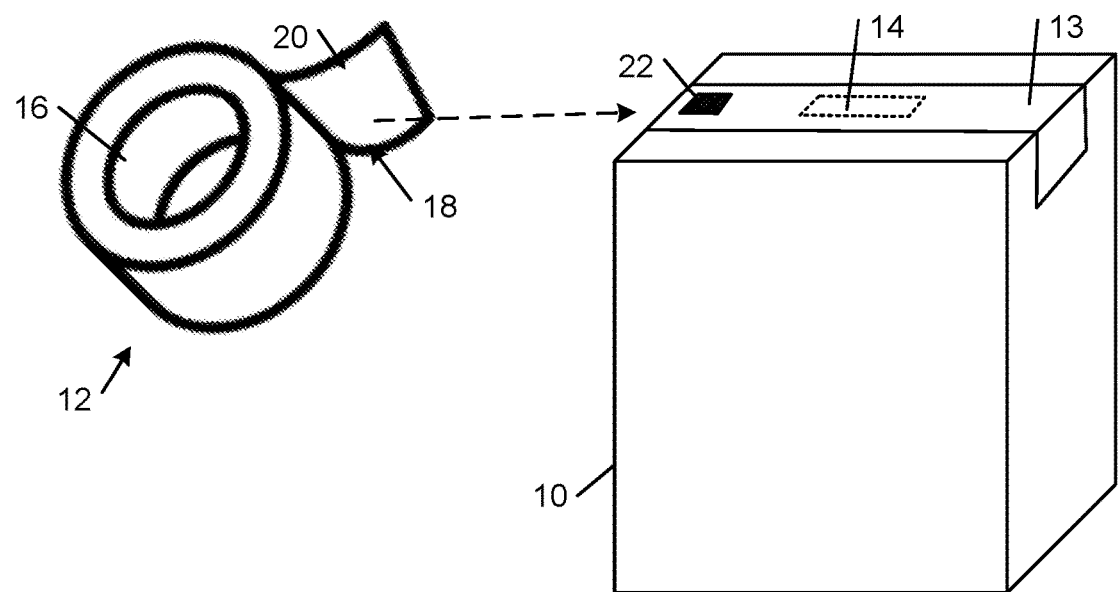
FIG. 1A is a diagrammatic view of an asset that has been sealed for shipment using a segment of an example adhesive tape platform dispensed from a roll, according to some embodiments.

In fast-paced environments such as hospitals, assets may be moved frequently throughout buildings, wards, or other sections of an area. It is valuable to track assets as movement occurs in order to ensure that assets are accounted for, e.g., are not lost or misrepresented as being in or out of use. However, because assets may be moved quickly and unpredictably, there are difficulties in optimizing power usage and accurate data collection for asset tracking.

A tracking device is attached to a mobile asset for tracking the location and/or condition of the mobile asset. The tracking device wirelessly communicates with one or more gateway nodes to determine a location, a direction of movement, and a most likely path of the mobile asset. The tracking device may be configured with different settings based on the most likely path. By updating the settings according to the most likely path, a tracking system may selectively increase the granularity or frequency of updates on the determined location of the mobile asset, which allows for improved tracking in critical areas of the system environment. By dynamically configuring the settings, efficient use of the tracking device's resources, such as battery life, may be maintained, without sacrificing crucial tracking data in areas or times of high important.

In some embodiments, the tracking device is an adhesive tape platform or a segment thereof. The adhesive tape platform includes wireless transducing components and circuitry that perform communication and/or sensing. The adhesive tape platform has a flexible adhesive tape form-factor that allows it to function as both an adhesive tape for adhering to and/or sealing objects and a wireless sensing device.

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements and are not drawn to scale.

As used herein, the term "or" refers to an inclusive "or" rather than an exclusive "or." In addition, the articles "a" and "an" as used in the specification and claims mean "one or more" unless specified otherwise or clear from the context to refer the singular form.

The term "tape node" refers to an adhesive tape platform or a segment thereof that is equipped with sensor, processor, memory, energy source/harvesting mechanism, and wireless communications functionality, where the adhesive tape platform (also referred to herein as an "adhesive product" or an "adhesive tape product") has a variety of different form factors, including a multilayer roll or a sheet that includes a plurality of divisible adhesive segments. Once deployed, each tape node can function, for example, as an adhesive tape, label, sticker, decal, or the like, and as a wireless communications device.

The terms "adhesive tape node," "wireless node," or "tape node" may be used interchangeably in certain contexts, and refer to an adhesive tape platform or a segment thereof that is equipped with sensor, processor, memory, energy source/ harvesting mechanism, and wireless communications functionality, where the adhesive product has a variety of different form factors, including a multilayer roll or a sheet that includes a plurality of divisible adhesive segments. Once deployed, each tape node or wireless node can function, for example, as an adhesive tape, label, sticker, decal, or the like, and as a wireless communications device. A "peripheral" tape node or wireless node, also referred to as an outer node, leaf node, or terminal node, refers to a node that does not have any child nodes.

In certain contexts, the terms "parcel," "envelope," "box," "package," "container," "pallet," "carton," "wrapping," and the like are used interchangeably herein to refer to a packaged item or items.

In certain contexts, the terms "wireless tracking system," "hierarchical communications network," "distributed agent operating system," and the like are used interchangeably herein to refer to a system or network of wireless nodes.

INTRODUCTION

This specification describes a low-cost, multi-function adhesive tape platform with a form factor that unobtrusively integrates the components useful for implementing a combination of different asset tracking and management functions and also is able to perform a useful ancillary function that otherwise would have to be performed with the attendant need for additional materials, labor, and expense. In an aspect, the adhesive tape platform is implemented as a collection of adhesive products that integrate wireless communications and sensing components within a flexible adhesive structure in a way that not only provides a cost-effective platform for interconnecting, optimizing, and protecting the components of the tracking system but also maintains the flexibility needed to function as an adhesive product that can be deployed seamlessly and unobtrusively into various asset management and tracking applications and workflows, including person and object tracking applications, and asset management workflows such as manufacturing, storage, shipping, delivery, and other logistics associated with moving products and other physical objects, including logistics, sensing, tracking, locationing, warehousing, parking, safety, construction, event detection, road management and infrastructure, security, and healthcare. In some examples, the adhesive tape platforms are used in various aspects of asset management, including sealing assets, transporting assets, tracking assets, monitoring the conditions of assets, inventorying assets, and verifying asset security. In these examples, the assets typically are transported from one location to another by truck, train, ship, or aircraft or within premises, e.g., warehouses by forklift, trolleys etc.

In disclosed examples, an adhesive tape platform includes a plurality of segments that can be separated from the adhesive product (e.g., by cutting, tearing, peeling, or the like) and adhesively attached to a variety of different surfaces to inconspicuously implement any of a wide variety of different wireless communications based network communications and transducing (e.g., sensing, actuating, etc.) applications. Examples of such applications include: event detection applications, monitoring applications, security applications, notification applications, and tracking applications, including inventory tracking, asset tracking, person tracking, animal (e.g., pet) tracking, manufactured parts tracking, and vehicle tracking. In example embodiments, each segment of an adhesive tape platform is equipped with an energy source, wireless communication functionality, transducing functionality, and processing functionality that enable the segment to perform one or more transducing functions and report the results to a remote server or other computer system directly or through a network of tapes. The components of the adhesive tape platform are encapsulated within a flexible adhesive structure that protects the components from damage while maintaining the flexibility needed to function as an adhesive tape (e.g., duct tape or a label) for use in various applications and workflows. In addition to single function applications, example embodiments also include multiple transducers (e.g., sensing and/or actuating transducers) that extend the utility of the platform by, for example, providing supplemental information and functionality relating characteristics of the state and or environment of, for example, an article, object, vehicle, or person, over time.

Systems and processes for fabricating flexible multifunction adhesive tape platforms in efficient and low-cost ways also are described. In addition to using roll-to-roll and/or sheet-to-sheet manufacturing techniques, the fabrication systems and processes are configured to optimize the placement and integration of components within the flexible adhesive structure to achieve high flexibility and ruggedness. These fabrication systems and processes are able to create useful and reliable adhesive tape platforms that can provide local sensing, wireless transmitting, and locationing functionalities. Such functionality together with the low cost of production is expected to encourage the ubiquitous deployment of adhesive tape platform segments and thereby alleviate at least some of the problems arising from gaps in conventional infrastructure coverage that prevent continuous monitoring, event detection, security, tracking, and other asset tracking and management applications across heterogeneous environments.

Adhesive Tape Platform

FIG. 1A shows an example asset 10 that is sealed for shipment using an example adhesive tape platform 12 that includes embedded components of a wireless transducing circuit 14 (collectively referred to herein as a "tape node"). In this example, a length 13 of the adhesive tape platform 12 is dispensed from a roll 16 and affixed to the asset 10. The adhesive tape platform 12 includes an adhesive side 18 and a non-adhesive side 20. The adhesive tape platform 12 can be dispensed from the roll 16 in the same way as any conventional packing tape, shipping tape, or duct tape. For example, the adhesive tape platform 12 may be dispensed from the roll 16 by hand, laid across the seam where the two top flaps of the asset 10 meet, and cut to a suitable length either by hand or using a cutting instrument (e.g., scissors or an automated or manual tape dispenser). Examples of such tapes include tapes having non-adhesive sides 20 that carry one or more coatings or layers (e.g., colored, light reflective, light absorbing, and/or light emitting coatings or layers).

Figure 1B:
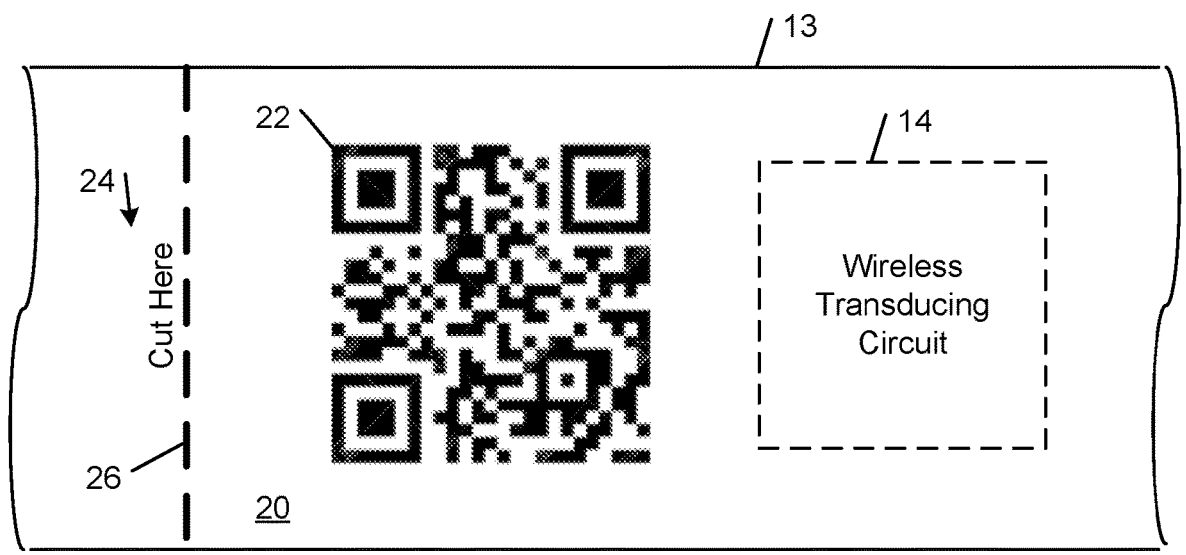
FIG. 1B is a diagrammatic top view of a portion of the segment of the example adhesive tape platform shown in FIG. 1A, according to some embodiments.

Referring to FIG. 1B, in some examples, the non-adhesive side 20 of the length 13 of the adhesive tape platform 12 includes writing or other markings that convey instructions, warnings, or other information to a person or machine (e.g., a bar code reader), or may simply be decorative and/or entertaining. For example, different types of adhesive tape platforms may be marked with distinctive colorations to distinguish one type of adhesive tape platform from another. In the illustrated example, the length 13 of the adhesive tape platform 12 includes a two-dimensional bar code (e.g., a QR Code) 22, written instructions 24 (i.e., "Cut Here"), and an associated cut line 26 that indicates where the user should cut the adhesive tape platform 12. The written instructions 24 and the cut line 26 typically are printed or otherwise marked on the top non-adhesive surface 20 of the adhesive tape platform 12 during manufacture. The two-dimensional bar code 22, on the other hand, may be marked on the non-adhesive surface 20 of the adhesive tape platform 12 during the manufacture of the adhesive product 12 or, alternatively, may be marked on the non-adhesive surface 20 of the adhesive tape platform 12 as needed using, for example, a printer or other marking device.

In order to avoid damage to the functionality of the segments of the adhesive tape platform 12, the cut lines 26 typically demarcate the boundaries between adjacent segments at locations that are free of any active components of the wireless transducing circuit 14. The spacing between the wireless transducing circuit components 14 and the cut lines 26 may vary depending on the intended communication, transducing and/or adhesive taping application. In the example illustrated in FIG. 1A, the length of the adhesive tape platform 12 that is dispensed to seal the asset 10 corresponds to a single segment of the adhesive tape platform 12. In other examples, the length of the adhesive tape platform 12 needed to seal a asset or otherwise serve the adhesive function for which the adhesive tape platform 12 is being applied may include multiple segments 13 of the adhesive tape platform 12, one or more of which segments 13 may be activated upon cutting the length of the adhesive tape platform 12 from the roll 16 and/or applying the length of the adhesive tape platform to the asset 10.

In some examples, the transducing components 14 that are embedded in one or more segments 13 of the adhesive tape platform 12 are activated when the adhesive tape platform 12 is cut along the cut line 26. In these examples, the adhesive tape platform 12 includes one or more embedded energy sources (e.g., thin film batteries, which may be printed, or conventional cell batteries, such as conventional watch style batteries, rechargeable batteries, or other energy storage device, such as a super capacitor or charge pump) that supply power to the transducing components 14 in one or more segments of the adhesive tape platform 12 in response to being separated from the adhesive tape platform 12 (e.g., along the cut line 26).

In some examples, each segment 13 of the adhesive tape platform 12 includes its own respective energy source including energy harvesting elements that can harvest energy from the environment. In some of these examples, each energy source is configured to only supply power to the components in its respective adhesive tape platform segment regardless of the number of contiguous segments 13 that are in a given length of the adhesive tape platform 12. In other examples, when a given length of the adhesive tape platform 12 includes multiple segments 13, the energy sources in the respective segments 13 are configured to supply power to the transducing components 14 in all of the segments 13 in the given length of the adhesive tape platform 12. In some of these examples, the energy sources are connected in parallel and concurrently activated to power the transducing components 14 in all of the segments 13 at the same time. In other examples, the energy sources are connected in parallel and alternately activated to power the transducing components 14 in respective ones of the adhesive tape platform segments 13 at different time periods, which may or may not overlap.

Figure 2:
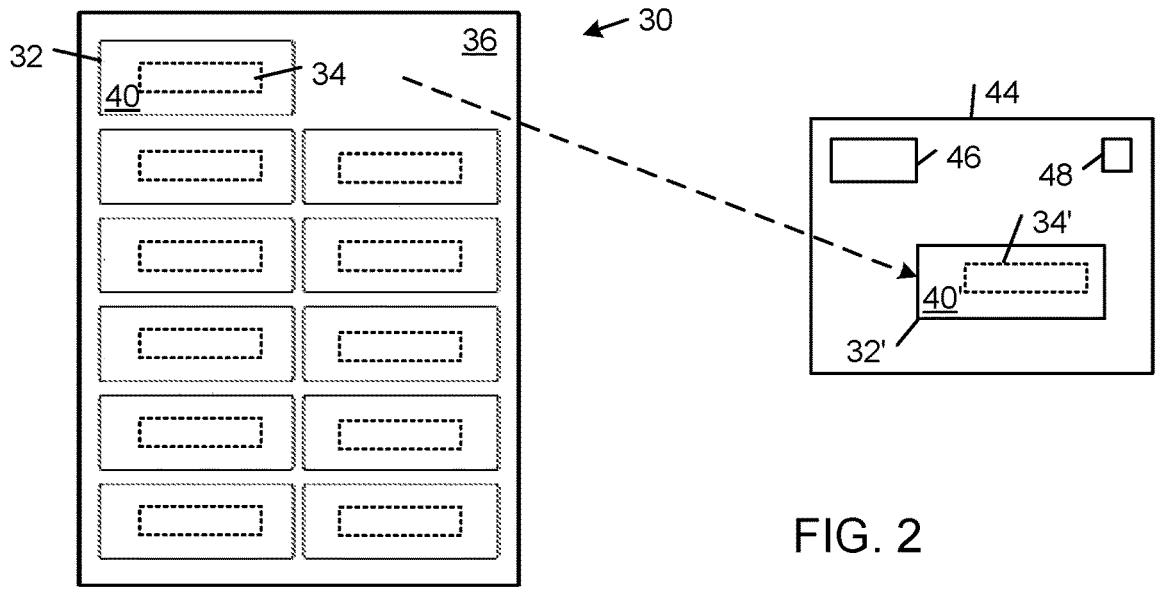
FIG. 2 is a diagrammatic view of an example of an envelope carrying a segment of an example adhesive tape platform dispensed from a backing sheet, according to some embodiments.

FIG. 2 shows an example adhesive tape platform 30 that includes a set of adhesive tape platform segments 32 each of which includes a respective set of embedded wireless transducing circuit components 34, and a backing sheet 36 with a release coating that prevents the adhesive segments 32 from adhering strongly to the backing sheet 36. Each adhesive tape platform segment 32 includes an adhesive side facing the backing sheet 36, and an opposing non-adhesive side 40. In this example, a particular segment 32' of the adhesive tape platform 30 has been removed from the backing sheet 36 and affixed to an envelope 44. Each segment 32 of the adhesive tape platform 30 can be removed from the backing sheet 36 in the same way that adhesive labels can be removed from a conventional sheet of adhesive labels (e.g., by manually peeling a segment 32 from the backing sheet 36). In general, the non-adhesive side 40' of the segment 32' may include any type of writing, markings, decorative designs, or other ornamentation. In the illustrated example, the non-adhesive side 40' of the segment 32' includes writing or other markings that correspond to a destination address for the envelope 44. The envelope 44 also includes a return address 46 and, optionally, a postage stamp or mark 48.

In some examples, segments of the adhesive tape platform 12 are deployed by a human operator. The human operator may be equipped with a mobile phone or other device that allows the operator to authenticate and initialize the adhesive tape platform 12. In addition, the operator can take a picture of a asset including the adhesive tape platform and any barcodes associated with the asset and, thereby, create a persistent record that links the adhesive tape platform 12 to the asset. In addition, the human operator typically will send the picture to a network service and/or transmit the picture to the adhesive tape platform 12 for storage in a memory component of the adhesive tape platform 12.

In some examples, the wireless transducing circuit components 34 that are embedded in a segment 32 of the adhesive tape platform 12 are activated when the segment 32 is removed from the backing sheet 32. In some of these examples, each segment 32 includes an embedded capacitive sensing system that can sense a change in capacitance when the segment 32 is removed from the backing sheet 36. As explained in detail below, a segment 32 of the adhesive tape platform 30 includes one or more embedded energy sources (e.g., thin film batteries, common disk-shaped cell batteries, or rechargeable batteries or other energy storage devices, such as a super capacitor or charge pump) that can be configured to supply power to the wireless transducing circuit components 34 in the segment 32 in response to the detection of a change in capacitance between the segment 32 and the backing sheet 36 as a result of removing the segment 32 from the backing sheet 36.

Figure 3:
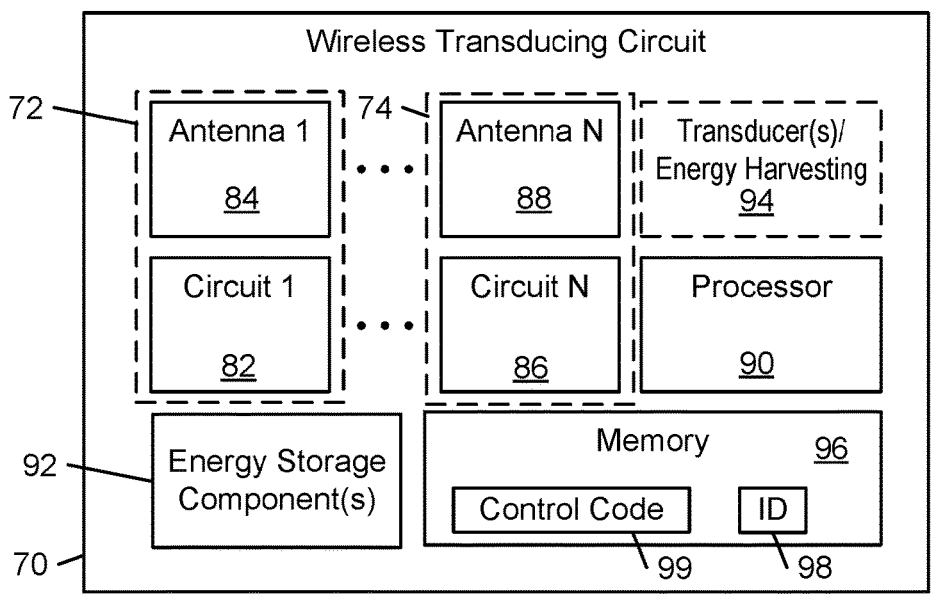
FIG. 3 is a schematic view of an example segment of an adhesive tape platform, according to some embodiments.

FIG. 3 shows a block diagram of the components of an example wireless transducing circuit 70 that includes a number of communication systems 72, 74. Example communication systems 72, 74 include a GPS system that includes a GPS receiver circuit 82 (e.g., a receiver integrated circuit) and a GPS antenna 84, and one or more wireless communication systems each of which includes a respective transceiver circuit 86 (e.g., a transceiver integrated circuit) and a respective antenna 88. Example wireless communication systems include a cellular communication system (e.g., GSM/GPRS), a Wi-Fi communication system, an RF communication system (e.g., LoRa), a Bluetooth communication system (e.g., a Bluetooth Low Energy, or BLE, system), a Z-wave communication system, and a ZigBee communication system. The wireless transducing circuit 70 also includes a processor 90 (e.g., a microcontroller or microprocessor), one or more energy storage devices 92 (e.g., non-rechargeable or rechargeable printed flexible battery, conventional single or multiple cell battery, and/or a super capacitor or charge pump), one or more transducers 94 (e.g., sensors and/or actuators, and, optionally, one or more energy harvesting transducer components). In some examples, the conventional single or multiple cell battery may be a watch style disk or button cell battery that is associated electrical connection apparatus (e.g., a metal clip) that electrically connects the electrodes of the battery to contact pads on the flexible circuit 116.

Examples of sensing transducers 94 include a capacitive sensor, an altimeter, a gyroscope, an accelerometer, a temperature sensor, a strain sensor, a pressure sensor, a piezoelectric sensor, a weight sensor, an optical or light sensor (e.g., a photodiode or a camera), an acoustic or sound sensor (e.g., a microphone), a smoke detector, a radioactivity sensor, a chemical sensor (e.g., an explosives detector), a biosensor (e.g., a blood glucose biosensor, odor detectors, antibody based pathogen, food, and water contaminant and toxin detectors, DNA detectors, microbial detectors, pregnancy detectors, and ozone detectors), a magnetic sensor, an electromagnetic field sensor, and a humidity sensor. Examples of actuating (e.g., energy emitting) transducers 94 include light emitting components (e.g., light emitting diodes and displays), electro-acoustic transducers (e.g., audio speakers), electric motors, and thermal radiators (e.g., an electrical resistor or a thermoelectric cooler).

In some examples, the wireless transducing circuit 70 includes a memory 96 for storing data, including, e.g., profile data, state data, event data, sensor data, localization data, security data, and one or more unique identifiers (ID) 98 associated with the wireless transducing circuit 70, such as a product ID, a type ID, and a media access control (MAC) ID, and control code 99. In some examples, the memory 96 may be incorporated into one or more of the processor 90 or transducers 94, or may be a separate component that is integrated in the wireless transducing circuit 70 as shown in FIG. 3. The control code typically is implemented as programmatic functions or program modules that control the operation of the wireless transducing circuit 70, including a tape node communication manager that manages the manner and timing of tape node communications, a tape node power manager that manages power consumption, and a tape node connection manager that controls whether connections with other tape nodes are secure connections or unsecure connections, and a tape node storage manager that securely manages the local data storage on the node. The tape node connection manager ensures the level of security required by the end application and supports various encryption mechanisms. The tape node power manager and tape communication manager work together to optimize the battery consumption for data communication. In some examples, execution of the control code by the different types of tape nodes described herein may result in the performance of similar or different functions.

Figure 4:
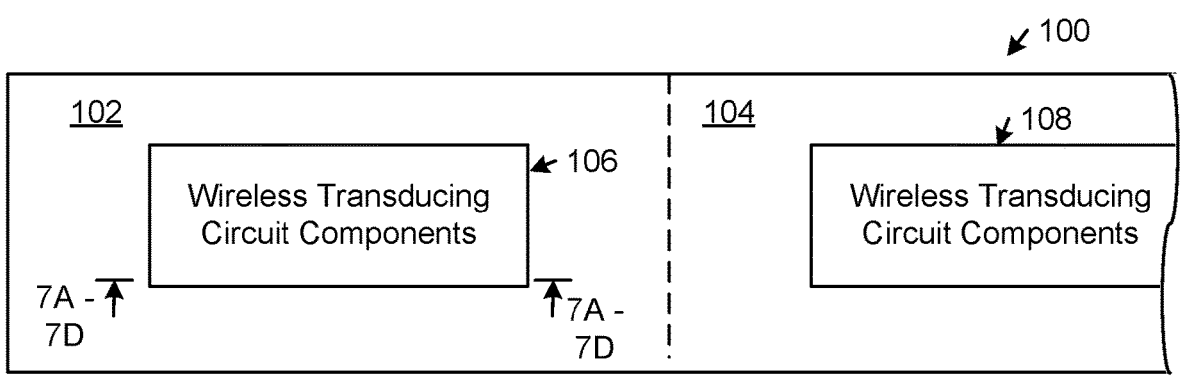
FIG. 4 is a diagrammatic top view of a length of an example adhesive tape platform, according to some embodiments.

FIG. 4 is a top view of a portion of an example flexible adhesive tape platform 100 that shows a first segment 102 and a portion of a second segment 104. Each segment 102, 104 of the flexible adhesive tape platform 100 includes a respective set 106, 108 of the components of the wireless transducing circuit 70. The segments 102, 104 and their respective sets of components 106, 108 typically are identical and configured in the same way. In some other embodiments, however, the segments 102, 104 and/or their respective sets of components 106, 108 are different and/or configured in different ways. For example, in some examples, different sets of the segments of the flexible adhesive tape platform 100 have different sets or configurations of tracking and/or transducing components that are designed and/or optimized for different applications, or different sets of segments of the flexible adhesive tape platform may have different ornamentations (e.g., markings on the exterior surface of the platform) and/or different (e.g., alternating) lengths.

An example method of fabricating the adhesive tape platform 100 (see FIG. 4) according to a roll-to-roll fabrication process is described in connection with FIGS. 6, 7A, and 7B of U.S. Pat. No. 10,262,255, issued Apr. 16, 2019, the entirety of which is incorporated herein by reference.

The instant specification describes an example system of adhesive tape platforms (also referred to herein as "tape nodes") that can be used to implement a low-cost wireless network infrastructure for performing monitoring, tracking, and other asset management functions relating to, for example, parcels, persons, tools, equipment and other physical assets and objects. The example system includes a set of three different types of tape nodes that have different respective functionalities and different respective cover markings that visually distinguish the different tape node types from one another. In one non-limiting example, the covers of the different tape node types are marked with different colors (e.g., white, green, and black). In the illustrated examples, the different tape node types are distinguishable from one another by their respective wireless communications capabilities and their respective sensing capabilities.

Figure 5A:
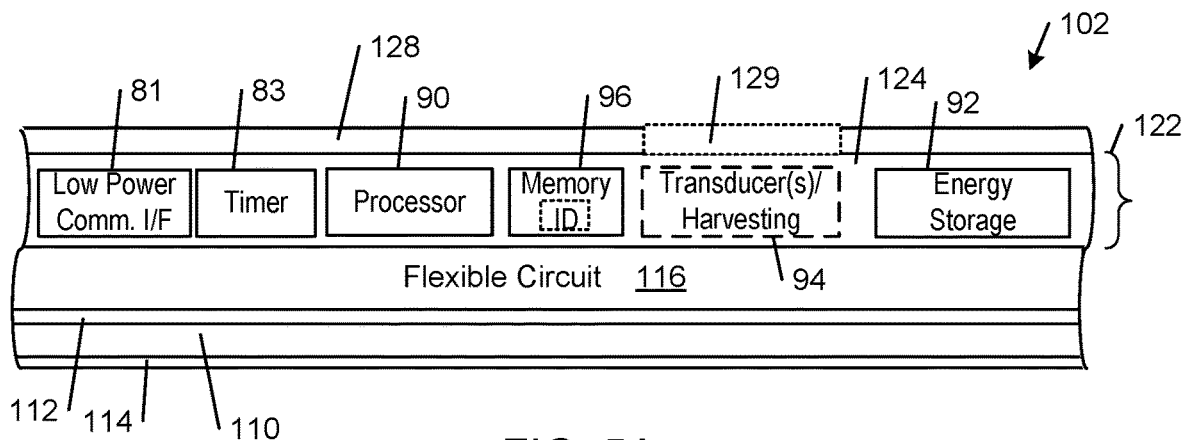
FIGS. 5A-5C show diagrammatic cross-sectional side views of portions of different respective adhesive tape platforms, according to some embodiments.

FIG. 5A shows a cross-sectional side view of a portion of an example segment 102 of the flexible adhesive tape platform 100 that includes a respective set of the components of the wireless transducing circuit 106 corresponding to the first tape node type (i.e., white). The flexible adhesive tape platform segment 102 includes an adhesive layer 112, an optional flexible substrate 110, and an optional adhesive layer 114 on the bottom surface of the flexible substrate 110. If the bottom adhesive layer 114 is present, a release liner (not shown) may be (weakly) adhered to the bottom surface of the adhesive layer 114. In some examples, the adhesive layer 114 includes an adhesive (e.g., an acrylic foam adhesive) that has a high bond strength that is sufficient to prevent removal of the adhesive segment 102 from a surface on which the adhesive layer 114 is adhered without destroying the physical or mechanical integrity of the adhesive segment 102 and/or one or more of its constituent components. In some examples, the optional flexible substrate 110 is implemented as a prefabricated adhesive tape that includes the adhesive layers 112, 114 and the optional release liner. In other examples, the adhesive layers 112, 114 are applied to the top and bottom surfaces of the flexible substrate 110 during the fabrication of the adhesive tape platform 100. The adhesive layer 112 bonds the flexible substrate 110 to a bottom surface of a flexible circuit 116, that includes one or more wiring layers (not shown) that connect the processor 90, a low power wireless communication interface 81 (e.g., a Zigbee, Bluetooth® Low Energy (BLE) interface, or other low power communication interface), a timer circuit 83, transducing and/or energy harvesting component(s) 94 (if present), the memory 96, and other components in a device layer 122 to each other and to the energy storage component 92 and, thereby, enable the transducing, tracking and other functionalities of the flexible adhesive tape platform segment 102. The low power wireless communication interface 81 typically includes one or more of the antennas 84, 88 and one or more of the wireless circuits 82, 86.

Figure 5B:
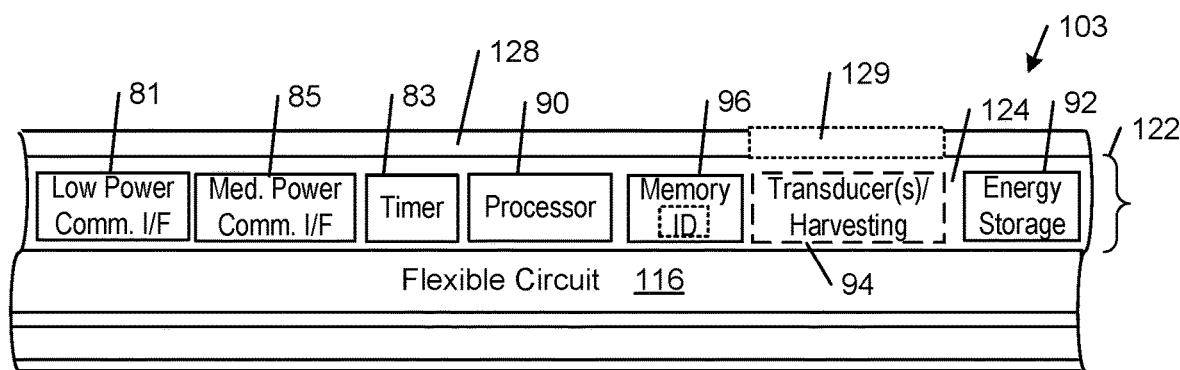

FIG. 5B shows a cross-sectional side view of a portion of an example segment 103 of the flexible adhesive tape platform 100 that includes a respective set of the components of the wireless transducing circuit 106 corresponding to the second tape node type (i.e., green). In this example, the flexible adhesive tape platform segment 103 differs from the segment 102 shown in FIG. 5A by the inclusion of a medium power communication interface 85 (e.g., a LoRa interface) in addition to the low power communications interface that is present in the first tape node type (i.e., white). The medium power communication interface has longer communication range than the low power communication interface. In some examples, one or more other components of the flexible adhesive tape platform segment 103 differ, for example, in functionality or capacity (e.g., larger energy source).

Figure 5C:
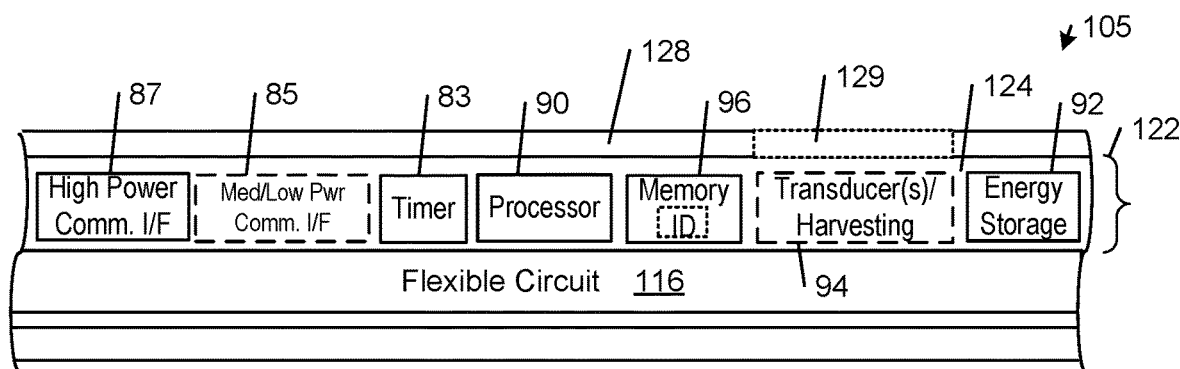

FIG. 5C shows a cross-sectional side view of a portion of an example segment 105 of the flexible adhesive tape platform 100 that includes a respective set of the components of the wireless transducing circuit 106 corresponding to the third tape node type (i.e., black). In this example, the flexible adhesive tape platform segment 105 includes a high power communications interface 87 (e.g., a cellular interface; e.g., GSM/GPRS) and an optional medium and/or low power communications interface 85. The high power communication range provides global coverage to available infrastructure (e.g. the cellular network). In some examples, one or more other components of the flexible adhesive tape platform segment 105 differ, for example, in functionality or capacity (e.g., larger energy source).

FIGS. 5A-5C show examples in which the cover layer 128 of the flexible adhesive tape platform 100 includes one or more interfacial regions 129 positioned over one or more of the transducers 94. In examples, one or more of the interfacial regions 129 have features, properties, compositions, dimensions, and/or characteristics that are designed to improve the operating performance of the platform 100 for specific applications. In some examples, the flexible adhesive tape platform 100 includes multiple interfacial regions 129 over respective transducers 94, which may be the same or different depending on the target applications. Example interfacial regions include an opening, an optically transparent window, and/or a membrane located in the interfacial region 129 of the cover 128 that is positioned over the one or more transducers and/or energy harvesting components 94. Additional details regarding the structure and operation of example interfacial regions 129 are described in U.S. Provisional Patent Application No. 62/680,716, filed Jun. 5, 2018, PCT Patent Application No. PCT/US2018/064919, filed Dec. 11, 2018, U.S. Pat. No. 10,885,420, issued Jan. 4, 2021, U.S. Pat. No. 10,902,310 issued Jan. 25, 2021, and U.S. Provisional Patent Application No. 62/670,712, filed May 11, 2018, all of which are incorporated herein in their entirety.

In some examples, a flexible polymer layer 124 encapsulates the device layer 122 and thereby reduces the risk of damage that may result from the intrusion of contaminants and/or liquids (e.g., water) into the device layer 122. The flexible polymer layer 124 also planarizes the device layer 122. This facilitates optional stacking of additional layers on the device layer 122 and also distributes forces generated in, on, or across the adhesive tape platform segment 102 so as to reduce potentially damaging asymmetric stresses that might be caused by the application of bending, torqueing, pressing, or other forces that may be applied to the flexible adhesive tape platform segment 102 during use. In the illustrated example, a flexible cover 128 is bonded to the planarizing polymer 124 by an adhesive layer (not shown).

The flexible cover 128 and the flexible substrate 110 may have the same or different compositions depending on the intended application. In some examples, one or both of the flexible cover 128 and the flexible substrate 110 include flexible film layers and/or paper substrates, where the film layers may have reflective surfaces or reflective surface coatings. Example compositions for the flexible film layers include polymer films, such as polyester, polyimide, polyethylene terephthalate (PET), and other plastics. The optional adhesive layer on the bottom surface of the flexible cover 128 and the adhesive layers 112, 114 on the top and bottom surfaces of the flexible substrate 110 typically include a pressure-sensitive adhesive (e.g., a silicon-based adhesive). In some examples, the adhesive layers are applied to the flexible cover 128 and the flexible substrate 110 during manufacture of the adhesive tape platform 100 (e.g., during a roll-to-roll or sheet-to-sheet fabrication process). In other examples, the flexible cover 128 may be implemented by a prefabricated single-sided pressure-sensitive adhesive tape and the flexible substrate 110 may be implemented by a prefabricated double-sided pressure-sensitive adhesive tape; both kinds of tape may be readily incorporated into a roll-to-roll or sheet-to-sheet fabrication process. In some examples, the flexible polymer layer 124 is composed of a flexible epoxy (e.g., silicone).

In some examples, the energy storage device 92 is a flexible battery that includes a printed electrochemical cell, which includes a planar arrangement of an anode and a cathode and battery contact pads. In some examples, the flexible battery may include lithium-ion cells or nickel-cadmium electro-chemical cells. The flexible battery typically is formed by a process that includes printing or laminating the electro-chemical cells on a flexible substrate (e.g., a polymer film layer). In some examples, other components may be integrated on the same substrate as the flexible battery. For example, the low power wireless communication interface 81 and/or the processor(s) 90 may be integrated on the flexible battery substrate. In some examples, one or more of such components also (e.g., the flexible antennas and the flexible interconnect circuits) may be printed on the flexible battery substrate.

In some examples, the flexible circuit 116 is formed on a flexible substrate by printing, etching, or laminating circuit patterns on the flexible substrate. In some examples, the flexible circuit 116 is implemented by one or more of a single-sided flex circuit, a double access or back bared flex circuit, a sculpted flex circuit, a double-sided flex circuit, a multi-layer flex circuit, a rigid flex circuit, and a polymer thick film flex circuit. A single-sided flexible circuit has a single conductor layer made of, for example, a metal or conductive (e.g., metal filled) polymer on a flexible dielectric film. A double access or back bared flexible circuit has a single conductor layer but is processed so as to allow access to selected features of the conductor pattern from both sides. A sculpted flex circuit is formed using a multi-step etching process that produces a flex circuit that has finished copper conductors that vary in thickness along their respective lengths. A multilayer flex circuit has three or more layers of conductors, where the layers typically are interconnected using plated through holes. Rigid flex circuits are a hybrid construction of flex circuit consisting of rigid and flexible substrates that are laminated together into a single structure, where the layers typically are electrically interconnected via plated through holes. In polymer thick film (PTF) flex circuits, the circuit conductors are printed onto a polymer base film, where there may be a single conductor layer or multiple conductor layers that are insulated from one another by respective printed insulating layers.

In the example flexible adhesive tape platform segments 102 shown in FIGS. 5A-5C, the flexible circuit 116 is a single access flex circuit that interconnects the components of the adhesive tape platform on a single side of the flexible circuit 116. In other examples, the flexible circuit 116 is a double access flex circuit that includes a front-side conductive pattern that interconnects the low power communications interface 81, the timer circuit 83, the processor 90, the one or more transducers 94 (if present), and the memory 96, and allows through-hole access (not shown) to a back-side conductive pattern that is connected to the flexible battery (not shown). In these examples, the front-side conductive pattern of the flexible circuit 116 connects the communications circuits 82, 86 (e.g., receivers, transmitters, and transceivers) to their respective antennas 84, 88 and to the processor 90, and also connects the processor 90 to the one or more sensors 94 and the memory 96. The backside conductive pattern connects the active electronics (e.g., the processor 90, the communications circuits 82, 86, and the transducers) on the front-side of the flexible circuit 116 to the electrodes of the flexible battery 116 via one or more through holes in the substrate of the flexible circuit 116.

Depending on the target application, the wireless transducing circuits 70 are distributed across the flexible adhesive tape platform 100 according to a specified sampling density, which is the number of wireless transducing circuits 70 for a given unit size (e.g., length or area) of the flexible adhesive tape platform 100. In some examples, a set of multiple flexible adhesive tape platforms 100 are provided that include different respective sampling densities in order to seal different asset sizes with a desired number of wireless transducing circuits 70. In particular, the number of wireless transducing circuits per asset size is given by the product of the sampling density specified for the adhesive tape platform and the respective size of the adhesive tape platform 100 needed to seal the asset. This allows an automated packaging system to select the appropriate type of flexible adhesive tape platform 100 to use for sealing a given asset with the desired redundancy (if any) in the number of wireless transducer circuits 70. In some example applications (e.g., shipping low value goods), only one wireless transducing circuit 70 is used per asset, whereas in other applications (e.g., shipping high value goods) multiple wireless transducing circuits 70 are used per asset. Thus, a flexible adhesive tape platform 100 with a lower sampling density of wireless transducing circuits 70 can be used for the former application, and a flexible adhesive tape platform 100 with a higher sampling density of wireless transducing circuits 70 can be used for the latter application. In some examples, the flexible adhesive tape platforms 100 are color-coded or otherwise marked to indicate the respective sampling densities with which the wireless transducing circuits 70 are distributed across the different types of adhesive tape platforms 100.

Figure 6A:
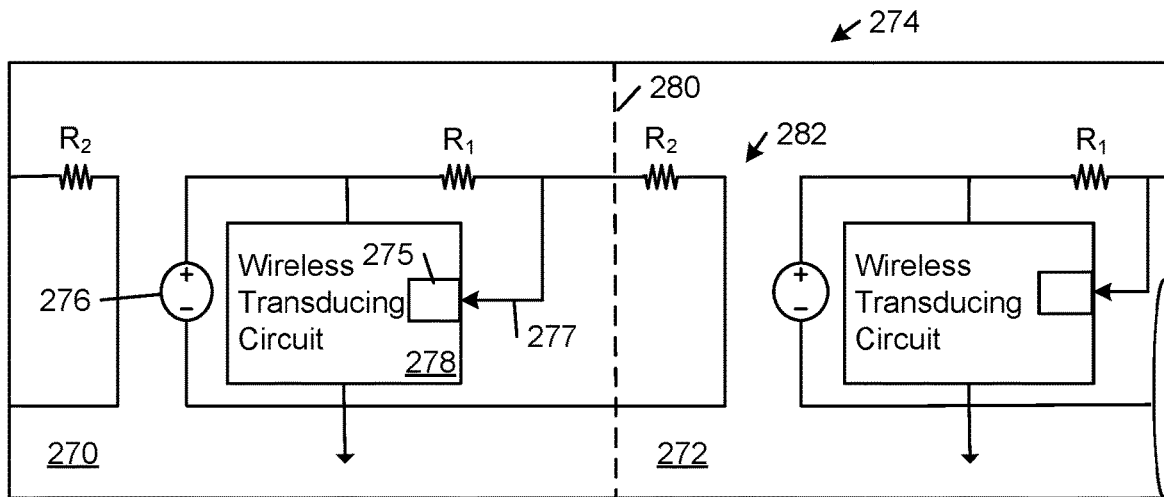
FIGS. 6A-6B are diagrammatic top views of a length of an example adhesive tape platform, according to some embodiments.

Referring to FIG. 6A, in some examples, each of one or more of the segments 270, 272 of a flexible adhesive tape platform 274 includes a respective one-time wake circuit 275 that delivers power from the respective energy source 276 to the respective wireless circuit 278 (e.g., a processor, one or more transducers, and one or more wireless communications circuits) in response to an event. In some of these examples, the wake circuit 275 is configured to transition from an off state to an on state when the voltage on the wake node 277 exceeds a threshold level, at which point the wake circuit transitions to an on state to power-on the segment 270. In the illustrated example, this occurs when the user separates the segment from the adhesive tape platform 274, for example, by cutting across the adhesive tape platform 274 at a designated location (e.g., along a designated cut-line 280). In particular, in its initial, un-cut state, a minimal amount of current flows through the resistors R1 and R2. As a result, the voltage on the wake node 277 remains below the threshold turn-on level. After the user cuts across the adhesive tape platform 274 along the designated cut-line 280, the user creates an open circuit in the loop 282, which pulls the voltage of the wake node above the threshold level and turns on the wake circuit 275. As a result, the voltage across the energy source 276 will appear across the wireless circuit 278 and, thereby, turn on the segment 270. In particular embodiments, the resistance value of resistor R1 is greater than the resistance value of R2. In some examples, the resistance values of resistors R1 and R2 are selected based on the overall design of the adhesive product system (e.g., the target wake voltage level and a target leakage current).

In some examples, each of one or more of the segments of an adhesive tape platform includes a respective sensor and a respective wake circuit that delivers power from the respective energy source to the respective one or more of the respective wireless circuit components 278 in response to an output of the sensor. In some examples, the respective sensor is a strain sensor that produces a wake signal based on a change in strain in the respective segment. In some of these examples, the strain sensor is affixed to a adhesive tape platform and configured to detect the stretching of the tracking adhesive tape platform segment as the segment is being peeled off a roll or a sheet of the adhesive tape platform. In some examples, the respective sensor is a capacitive sensor that produces a wake signal based on a change in capacitance in the respective segment. In some of these examples, the capacitive sensor is affixed to an adhesive tape platform and configured to detect the separation of the tracking adhesive tape platform segment from a roll or a sheet of the adhesive tape platform. In some examples, the respective sensor is a flex sensor that produces a wake signal based on a change in curvature in the respective segment. In some of these examples, the flex sensor is affixed to a adhesive tape platform and configured to detect bending of the tracking adhesive tape platform segment as the segment is being peeled off a roll or a sheet of the adhesive tape platform. In some examples, the respective sensor is a near field communications sensor that produces a wake signal based on a change in inductance in the respective segment.

Figure 6B:
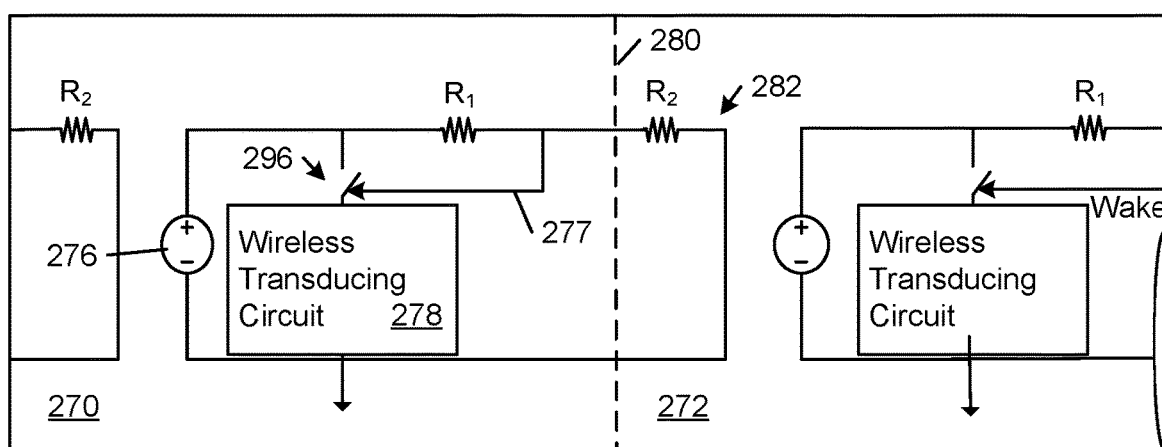

FIG. 6B shows another example of an adhesive tape platform 294 that delivers power from the respective energy source 276 to the respective tracking circuit 278 (e.g., a processor, one or more transducers, and one or more wireless communications circuits) in response to an event. This example is similar in structure and operation as the adhesive tape platform 294 shown in FIG. 6A, except that the wake circuit 275 is implemented by a switch 296 that is configured to transition from an open state to a closed state when the voltage on the switch node 277 exceeds a threshold level. In the initial state of the adhesive tape platform 294, the voltage on the switch node is below the threshold level as a result of the low current level flowing through the resistors R1 and R2. After the user cuts across the adhesive tape platform 294 along the designated cut-line 280, the user creates an open circuit in the loop 282, which pulls up the voltage on the switch node above the threshold level to close the switch 296 and turn on the wireless circuit 278.

Figure 6C:
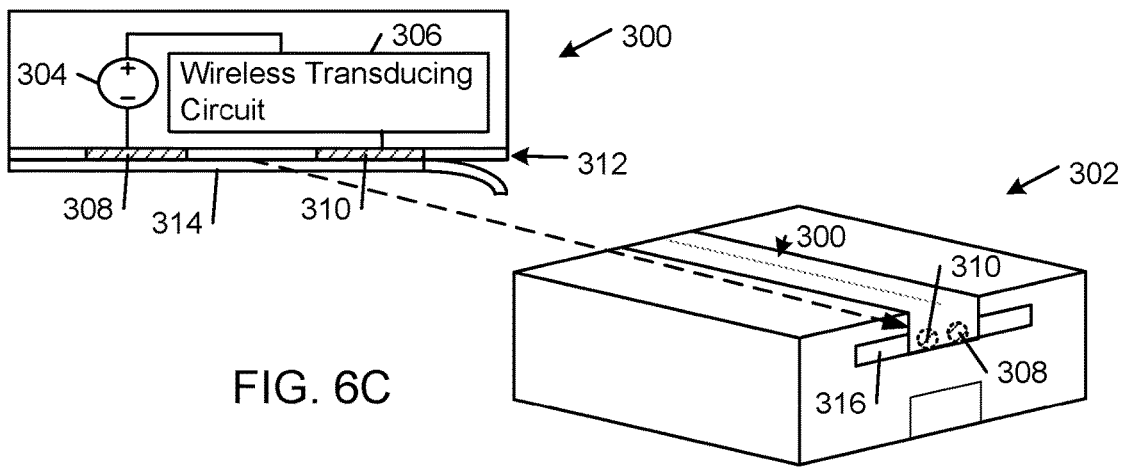
FIG. 6C is a diagrammatic view of a length of an example adhesive tape platform adhered to an asset, according to some embodiments.

FIG. 6C shows a diagrammatic cross-sectional front view of an example adhesive tape platform 300 and a perspective view of an example asset 302. Instead of activating the adhesive tape platform in response to separating a segment of the adhesive tape platform from a roll or a sheet of the adhesive tape platform, this example is configured to supply power from the energy source 302 to turn on the wireless transducing circuit 306 in response to establishing an electrical connection between two power terminals 308, 310 that are integrated into the adhesive tape platform. In particular, each segment of the adhesive tape platform 300 includes a respective set of embedded tracking components, an adhesive layer 312, and an optional backing sheet 314 with a release coating that prevents the segments from adhering strongly to the backing sheet 314. In some examples, the power terminals 308, 310 are composed of an electrically conductive material (e.g., a metal, such as copper) that may be printed or otherwise patterned and/or deposited on the backside of the adhesive tape platform 300. In operation, the adhesive tape platform can be activated by removing the backing sheet 314 and applying the exposed adhesive layer 312 to a surface that includes an electrically conductive region 316. In the illustrated embodiment, the electrically conductive region 316 is disposed on a portion of the asset 302. When the adhesive backside of the adhesive tape platform 300 is adhered to the asset with the exposed terminals 308, 310 aligned and in contact with the electrically conductive region 316 on the asset 302, an electrical connection is created through the electrically conductive region 316 between the exposed terminals 308, 310 that completes the circuit and turns on the wireless transducing circuit 306. In particular embodiments, the power terminals 308, 310 are electrically connected to any respective nodes of the wireless transducing circuit 306 that would result in the activation of the tracking circuit 306 in response to the creation of an electrical connection between the power terminals 308, 310.

In some examples, after a tape node is turned on, it will communicate with the network service to confirm that the user/operator who is associated with the tape node is an authorized user who has authenticated himself or herself to the network service 54. In these examples, if the tape node cannot confirm that the user/operator is an authorized user, the tape node will turn itself off.

Deployment of Tape Nodes

Figure 7:
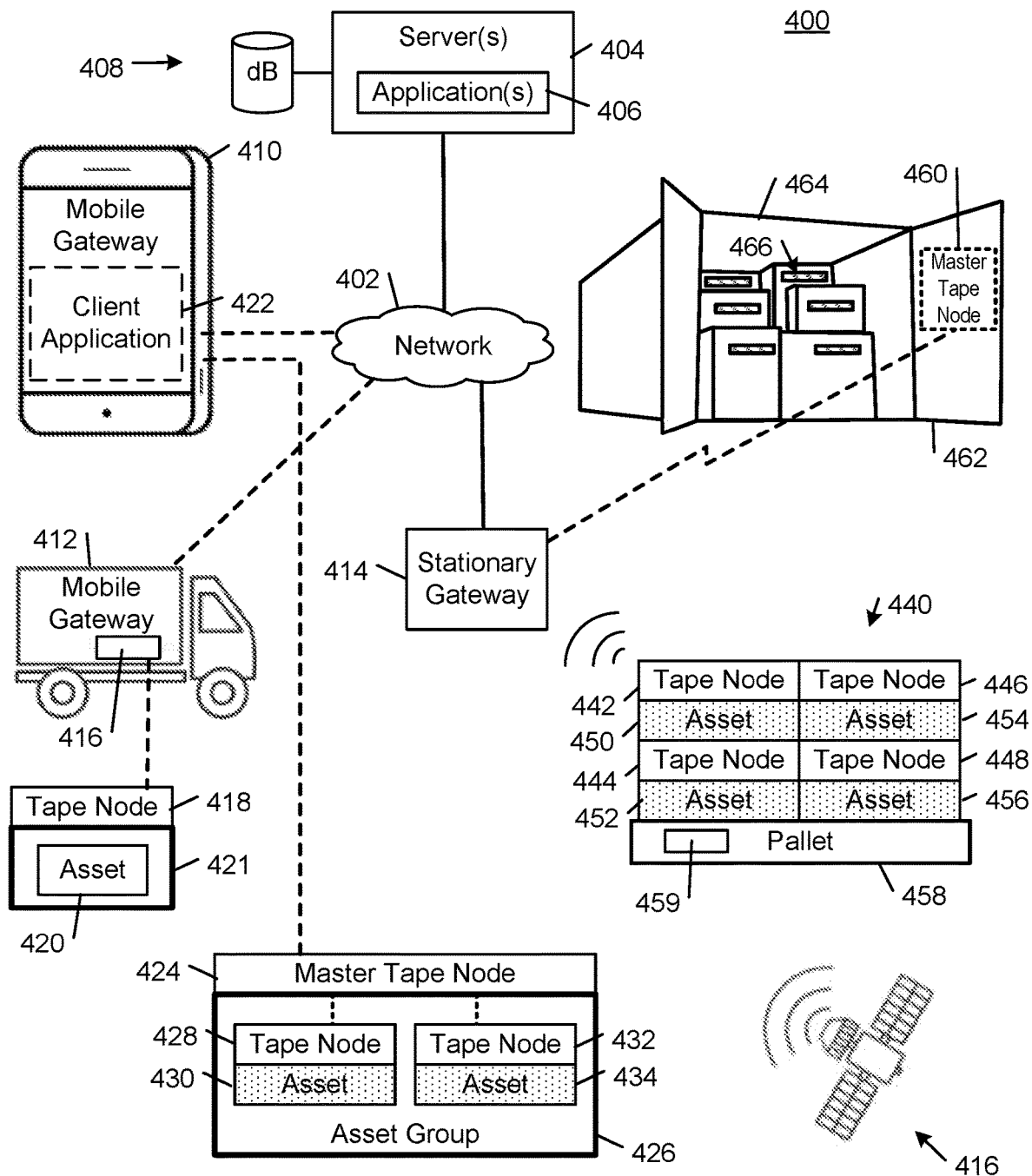
FIG. 7 is a diagrammatic view of an example of a network environment supporting communications with segments of an adhesive tape platform, according to some embodiments.

FIG. 7 shows an example network communications environment 400 (also referred to herein as an "IOT system" 400 or "tracking system" 400) that includes a network 402 that supports communications between one or more servers 404 executing one or more applications of a network service 408, mobile gateways 410, 412, a stationary gateway 414, and various types of tape nodes that are associated with various assets (e.g., parcels, equipment, tools, persons, and other things). Each member of the IOT system 400 may be referred to as a node of the IOT system 400, including the tape nodes, other wireless IOT devices, gateways (stationary and mobile), client devices, and servers. In some examples, the network 402 includes one or more network communication systems and technologies, including any one or more of wide area networks, local area networks, public networks (e.g., the internet), private networks (e.g., intranets and extranets), wired networks, and wireless networks. For example, the network 402 includes communications infrastructure equipment, such as a geolocation satellite system 416 (e.g., GPS, GLONASS, and NAVSTAR), cellular communication systems (e.g., GSM/GPRS), Wi-Fi communication systems, RF communication systems (e.g., LoRa), Bluetooth communication systems (e.g., a Bluetooth Low Energy system), Z-wave communication systems, and ZigBee communication systems.

In some examples, the one or more network service applications 406 leverage the above-mentioned communications technologies to create a hierarchical wireless network of tape nodes that improves asset management operations by reducing costs and improving efficiency in a wide range of processes, from asset packaging, asset transporting, asset tracking, asset condition monitoring, asset inventorying, and asset security verification. Communication across the network is secured by a variety of different security mechanisms. In the case of existing infrastructure, a communication link the communication uses the infrastructure security mechanisms. In case of communications among tapes nodes, the communication is secured through a custom security mechanism. In certain cases, tape nodes can also be configured to support block chain to protect the transmitted and stored data.

A set of tape nodes can be configured by the network service 408 to create hierarchical communications network. The hierarchy can be defined in terms of one or more factors, including functionality (e.g., wireless transmission range or power), role (e.g., master tape node vs. peripheral tape node), or cost (e.g., a tape node equipped with a cellular transceiver vs. a peripheral tape node equipped with a Bluetooth LE transceiver). Tape nodes can be assigned to different levels of a hierarchical network according to one or more of the above-mentioned factors. For example, the hierarchy can be defined in terms of communication range or power, where tape nodes with higher power or longer communication range transceivers are arranged at a higher level of the hierarchy than tape nodes with lower power or lower range transceivers. In another example, the hierarchy is defined in terms of role, where, e.g., a master tape node is programmed to bridge communications between a designated group of peripheral tape nodes and a gateway node or server node. The problem of finding an optimal hierarchical structure can be formulated as an optimization problem with battery capacity of nodes, power consumption in various modes of operation, desired latency, external environment, etc. and can be solved using modern optimization methods e.g. neural networks, artificial intelligence, and other machine learning computing systems that take expected and historical data to create an optimal solution and can create algorithms for modifying the system's behavior adaptively in the field.

The tape nodes may be deployed by automated equipment or manually. In this process, a tape node typically is separated from a roll or sheet and adhered to a asset, or other stationary or mobile object (e.g., a structural element of a warehouse, or a vehicle, such as a delivery truck) or stationary object (e.g., a structural element of a building). This process activates the tape node and causes the tape node to communicate with a server 404 of the network service 408. In this process, the tape node may communicate through one or more other tape nodes in the communication hierarchy. In this process, the network server 404 executes the network service application 406 to programmatically configure tape nodes that are deployed in the environment 400. In some examples, there are multiple classes or types of tape nodes, where each tape node class has a different respective set of functionalities and/or capacities.

In some examples, the one or more network service servers 404 communicate over the network 402 with one or more gateways that are configured to send, transmit, forward, or relay messages to the network 402 and activated tape nodes that are associated with respective assets and within communication range. Example gateways include mobile gateways 410, 412 and a stationary gateway 414. In some examples, the mobile gateways 410, 412, and the stationary gateway 414 are able to communicate with the network 402 and with designated sets or groups of tape nodes.

In some examples, the mobile gateway 412 is a vehicle (e.g., a delivery truck or other mobile hub) that includes a wireless communications unit 416 that is configured by the network service 408 to communicate with a designated set of tape nodes, including a peripheral tape node 418 in the form of a label that is adhered to an asset 420 contained within a parcel 421 (e.g., an envelope), and is further configured to communicate with the network service 408 over the network 402. In some examples, the peripheral tape node 418 includes a lower power wireless communications interface of the type used in, e.g., tape node 102 (shown in FIG. 5A), and the wireless communications unit 416 is implemented by a tape node (e.g., one of tape node 103 or tape node 105, respectively shown in FIGS. 5B and 5C) that includes a lower power communications interface for communicating with tape nodes within range of the mobile gateway 412 and a higher power communications interface for communicating with the network 402. In this way, the tape nodes 418 and 416 create a hierarchical wireless network of nodes for transmitting, forwarding, bridging, relaying, or otherwise communicating wireless messages to, between, or on behalf of the peripheral tape node 418 and the network service 408 in a power-efficient and cost-effective way.

In some examples, the mobile gateway 410 is a mobile phone that is operated by a human operator and executes a client application 422 that is configured by the network service 408 to communicate with a designated set of tape nodes, including a master tape node 424 that is adhered to a parcel 426 (e.g., a box), and is further configured to communicate with the network service 408 over the network 402. In the illustrated example, the parcel 426 contains a first parcel labeled or sealed by a tape node 428 and containing a first asset 430, and a second parcel labeled or sealed by a tape node 432 and containing a second asset 434. As explained in detail below, the master tape node 424 communicates with each of the peripheral tape nodes 428, 432 and communicates with the mobile gateway 408 in accordance with a hierarchical wireless network of tape nodes. In some examples, each of the peripheral tape nodes 428, 432 includes a lower power wireless communications interface of the type used in, e.g., tape node 102 (shown in FIG. 5A), and the master tape node 424 is implemented by a tape node (e.g., tape node 103, shown in FIG. 5B) that includes a lower power communications interface for communicating with the peripheral tape nodes 428, 432 contained within the parcel 426, and a higher power communications interface for communicating with the mobile gateway 410. The master tape node 424 is operable to relay wireless communications between the tape nodes 428, 432 contained within the parcel 426 and the mobile gateway 410, and the mobile gateway 410 is operable to relay wireless communications between the master tape node 424 and the network service 408 over the wireless network 402. In this way, the master tape node 424 and the peripheral tape nodes 428 and 432 create a hierarchical wireless network of nodes for transmitting, forwarding, relaying, or otherwise communicating wireless messages to, between, or on behalf of the peripheral tape nodes 428, 432 and the network service 408 in a power-efficient and cost-effective way.

In some examples, the stationary gateway 414 is implemented by a server executing a server application that is configured by the network service 408 to communicate with a designated set 440 of tape nodes 442, 444, 446, 448 that are adhered to respective parcels containing respective assets 450, 452, 454, 456 on a pallet 458. In other examples, the stationary gateway 414 is implemented by a tape node (e.g., one of tape node 103 or tape node 105, respectively shown in FIGS. 5B and 5C) that is adhered to, for example, a wall, column or other infrastructure component of the environment 400, and includes a lower power communications interface for communicating with tape nodes within range of the stationary gateway 414 and a higher power communications interface for communicating with the network 402. In one embodiment, each of the tape nodes 442-448 is a peripheral tape node and is configured by the network service 408 to communicate individually with the stationary gateway 414, which relays communications from the tape nodes 442-448 to the network service 408 through the stationary gateway 414 and over the communications network 402. In another embodiment, one of the tape nodes 442-448 at a time is configured as a master tape node that transmits, forwards, relays, or otherwise communicate wireless messages to, between, or on behalf of the other tape nodes on the pallet 458. In this embodiment, the master tape node may be determined by the tape nodes 442-448 or designated by the network service 408. In some examples, the tape node with the longest range or highest remaining power level is determined to be the master tape node. In some examples, when the power level of the current master tape node drops below a certain level (e.g., a fixed power threshold level or a threshold level relative to the power levels of one or more of the other tape nodes), another one of the tape nodes assumes the role of the master tape node. In some examples, a master tape node 459 is adhered to the pallet 458 and is configured to perform the role of a master node for the tape nodes 442-448. In these ways, the tape nodes 442-448, 458 are configurable to create different hierarchical wireless networks of nodes for transmitting, forwarding, relaying, bridging, or otherwise communicating wireless messages with the network service 408 through the stationary gateway 414 and over the network 402 in a power-efficient and cost-effective way.

In the illustrated example, the stationary gateway 414 also is configured by the network service 408 to communicate with a designated set of tape nodes, including a master tape node 460 that is adhered to the inside of a door 462 of a shipping container 464, and is further configured to communicate with the network service 408 over the network 402. In the illustrated example, the shipping container 464 contains a number of parcels labeled or sealed by respective peripheral tape nodes 466 and containing respective assets. The master tape node 416 communicates with each of the peripheral tape nodes 466 and communicates with the stationary gateway 415 in accordance with a hierarchical wireless network of tape nodes. In some examples, each of the peripheral tape nodes 466 includes a lower power wireless communications interface of the type used in, e.g., tape node 102 (shown in FIG. 5A), and the master tape node 460 is implemented by a tape node (e.g., tape node 103, shown in FIG. 5B) that includes a lower power communications interface for communicating with the peripheral tape nodes 466 contained within the shipping container 464, and a higher power communications interface for communicating with the stationary gateway 414.

In some examples, when the doors of the shipping container 464 are closed, the master tape node 460 is operable to communicate wirelessly with the peripheral tape nodes 466 contained within the shipping container 464. In an example, the master tape node 460 is configured to collect sensor data from the peripheral tape nodes and, in some embodiments, process the collected data to generate, for example, one or more histograms from the collected data. When the doors of the shipping container 464 are open, the master tape node 460 is programmed to detect the door opening (e.g., with an accelerometer component of the master tape node 460) and, in addition to reporting the door opening event to the network service 408, the master tape node 460 is further programmed to transmit the collected data and/or the processed data in one or more wireless messages to the stationary gateway 414. The stationary gateway 414, in turn, is operable to transmit the wireless messages received from the master tape node 460 to the network service 408 over the wireless network 402. Alternatively, in some examples, the stationary gateway 414 also is operable to perform operations on the data received from the master tape node 460 with the same type of data produced by the master node 459 based on sensor data collected from the tape nodes 442-448. In this way, the master tape node 460 and the peripheral tape nodes 466 create a hierarchical wireless network of nodes for transmitting, forwarding, relaying, or otherwise communicating wireless messages to, between, or on behalf of the peripheral tape nodes 466 and the network service 408 in a power-efficient and cost-effective way.

In an example of the embodiment shown in FIG. 7, there are three classes of tape nodes: a short range tape node, a medium range tape node, and a long range tape node, as respectively shown in FIGS. 5A-5C. The short range tape nodes typically are adhered directly to parcels containing assets. In the illustrated example, the tape nodes 418, 428, 432, 442-448, 466 are short range tape nodes. The short range tape nodes typically communicate with a low power wireless communication protocol (e.g., Bluetooth LE, Zigbee, or Z-wave). The medium range tape nodes typically are adhered to objects (e.g., a box 426 and a shipping container 460) that are associated with multiple parcels that are separated from the medium range tape nodes by a barrier or a large distance. In the illustrated example, the tape nodes 424 and 460 are medium range tape nodes. The medium range tape nodes typically communicate with a medium power wireless communication protocol (e.g., LoRa or Wi-Fi). The long-range tape nodes typically are adhered to mobile or stationary infrastructure of the wireless communication environment 400. In the illustrated example, the mobile gateway tape node 412 and the stationary gateway tape node 414 are long range tape nodes. The long range tape nodes typically communicate with other nodes using a high power wireless communication protocol (e.g., a cellular data communication protocol). In some examples, the mobile gateway tape node 436 is adhered to a mobile vehicle (e.g., a truck). In these examples, the mobile gateway 412 may be moved to different locations in the environment 400 to assist in connecting other tape nodes to the server 404. In some examples, the stationary gateway tape node 414 may be attached to a stationary structure (e.g., a wall) in the environment 400 with a known geographic location. In these examples, other tape nodes in the environment can determine their geographic location by querying the gateway tape node 414.

Wireless Communications Network

Figure 8:
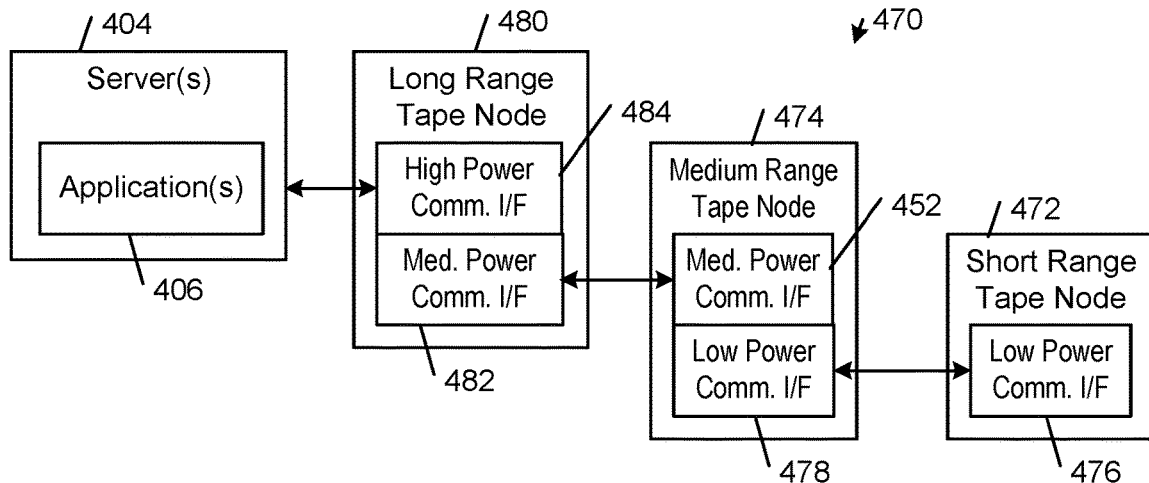
FIG. 8 is a diagrammatic view of a hierarchical communications network, according to some embodiments.

FIG. 8 shows an example hierarchical wireless communications network of tape nodes 470. In this example, the short range tape node 472 and the medium range tape node 474 communicate with one another over their respective low power wireless communication interfaces 476, 478. The medium range tape node 474 and the long range tape node 480 communicate with one another over their respective medium power wireless communication interfaces 478, 482. The long range tape node 480 and the network server 404 communicate with one another over the high power wireless communication interface 484. In some examples, the low power communication interfaces 476, 478 establish wireless communications with one another in accordance with the Bluetooth LE protocol, the medium power communication interfaces 452, 482 establish wireless communications with one another in accordance with the LoRa communications protocol, and the high power communication interface 484 establishes wireless communications with the server 404 in accordance with a cellular communications protocol.

In some examples, the different types of tape nodes are deployed at different levels in the communications hierarchy according to their respective communications ranges, with the long range tape nodes generally at the top of the hierarchy, the medium range tape nodes generally in the middle of the hierarchy, and the short range tape nodes generally at the bottom of the hierarchy. In some examples, the different types of tape nodes are implemented with different feature sets that are associated with component costs and operational costs that vary according to their respective levels in the hierarchy. This allows system administrators flexibility to optimize the deployment of the tape nodes to achieve various objectives, including cost minimization, asset tracking, asset localization, and power conservation.

In some examples, a server 404 of the network service 408 designates a tape node at a higher level in a hierarchical communications network as a master node of a designated set of tape nodes at a lower level in the hierarchical communications network. For example, the designated master tape node may be adhered to a parcel (e.g., a box, pallet, or shipping container) that contains one or more tape nodes that are adhered to one or more assets containing respective assets. In order to conserve power, the tape nodes typically communicate according to a schedule promulgated by the server 404 of the network service 408. The schedule usually dictates all aspects of the communication, including the times when particular tape nodes should communicate, the mode of communication, and the contents of the communication. In one example, the server 404 transmits programmatic Global Scheduling Description Language (GSDL) code to the master tape node and each of the lower-level tape nodes in the designated set. In this example, execution of the GSDL code causes each of the tape nodes in the designated set to connect to the master tape node at a different respective time that is specified in the GSDL code, and to communicate a respective set of one or more data packets of one or more specified types of information over the respective connection. In some examples, the master tape node simply forwards the data packets to the server network node 404, either directly or indirectly through a gateway tape node (e.g., the long range tape node 416 adhered to the mobile vehicle 412 or the long range tape node 414 adhered to an infrastructure component of the environment 400). In other examples, the master tape node processes the information contained in the received data packets and transmits the processed information to the server network node 404.

Figure 9:
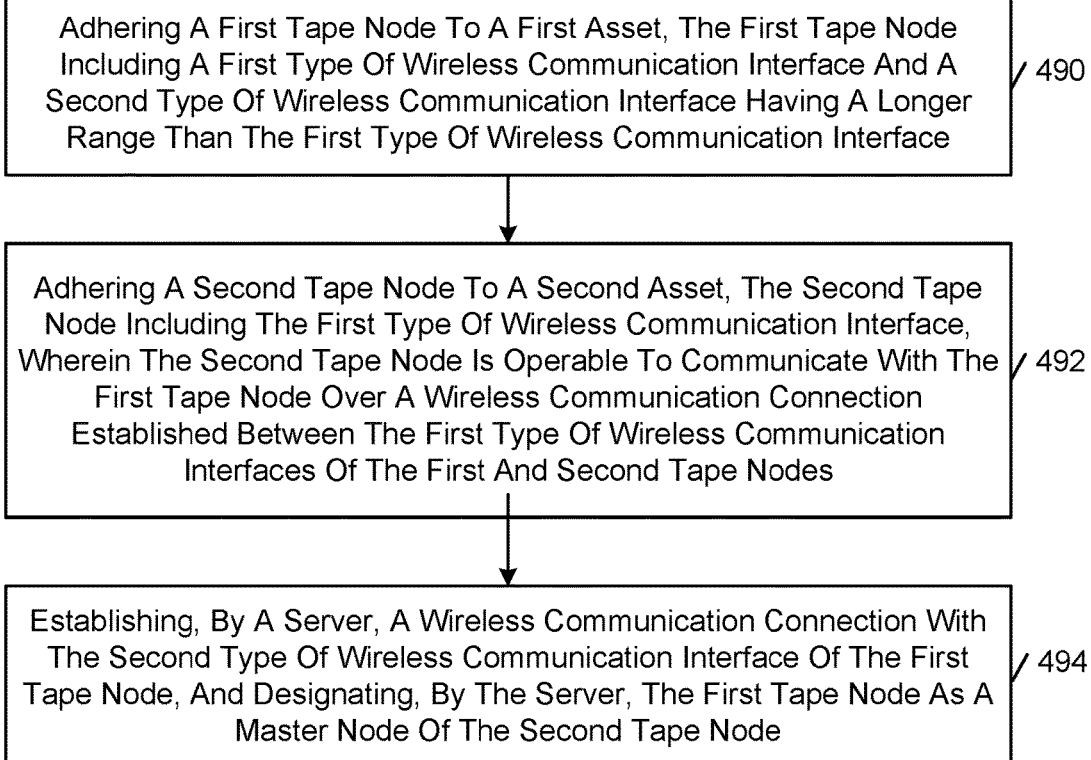
FIG. 9 is a flow diagram of a method of creating a hierarchical communications network, according to some embodiments.

FIG. 9 shows an example method of creating a hierarchical communications network. In accordance with this method, a first tape node is adhered to a first asset in a set of associated assets, the first tape node including a first type of wireless communication interface and a second type of wireless communication interface having a longer range than the first type of wireless communication interface (FIG. 9, block 490). A second tape node is adhered to a second asset in the set, the second tape node including the first type of wireless communication interface, wherein the second tape node is operable to communicate with the first tape node over a wireless communication connection established between the first type of wireless communication interfaces of the first and second tape nodes (FIG. 9, block 492). An application executing on a computer system (e.g., a server 404 of a network service 408) establishes a wireless communication connection with the second type of wireless communication interface of the first tape node, and the application transmits programmatic code executable by the first tape node to function as a master tape node with respect to the second tape node (FIG. 9, block 494).

In other embodiments, the second tape node is assigned the role of the master node of the first tape node.

Distributed Agent Operating System

As used herein, the term "node" refers to both a tape node and a non-tape node (i.e., a node or wireless device that is not an adhesive tape platform) unless the node is explicitly designated as a "tape node" or a "non-tape node." In some embodiments, a non-tape node may have the same or similar communication, sensing, processing and other functionalities and capabilities as the tape nodes described herein, except without being integrated into a tape platform. In some embodiments, non-tape nodes can interact seamlessly with tape nodes. Each node may be assigned a respective unique identifier, according to some embodiments.

The following disclosure describes a distributed software operating system that is implemented by distributed hardware nodes executing intelligent agent software to perform various tasks or algorithms. In some embodiments, the operating system distributes functionalities (e.g., performing analytics on data or statistics collected or generated by nodes) geographically across multiple intelligent agents that are bound to items (e.g., parcels, containers, packages, boxes, pallets, a loading dock, a door, a light switch, a vehicle such as a delivery truck, a shipping facility, a port, a hub, etc.). In addition, the operating system dynamically allocates the hierarchical roles (e.g., master and slave roles) that nodes perform over time in order to improve system performance, such as optimizing battery life across nodes, improving responsiveness, and achieving overall objectives. In some embodiments, optimization is achieved using a simulation environment for optimizing key performance indicators (PKIs).

In some embodiments, the nodes are programmed to operate individually or collectively as autonomous intelligent agents. In some embodiments, nodes are configured to communicate and coordinate actions and respond to events. In some embodiments, a node is characterized by its identity, its mission, and the services that it can provide to other nodes. A node's identity is defined by its capabilities (e.g., battery life, sensing capabilities, and communications interfaces). A node's mission (or objective) is defined by the respective program code, instructions, or directives it receives from another node (e.g., a server or a master node) and the actions or tasks that it performs in accordance with that program code, instructions, or directives (e.g., sense temperature every hour and send temperature data to a master node to upload to a server). A node's services define the functions or tasks that it is permitted to perform for other nodes (e.g., retrieve temperature data from a peripheral node and send the received temperature data to the server). At least for certain tasks, once programmed and configured with their identities, missions, and services, nodes can communicate with one another and request services from and provide services to one another independently of the server.

Thus, in accordance with the runtime operating system every agent knows its objectives (programmed). Every agent knows which capabilities/resources it needs to fulfill objective. Every agent communicates with every other node in proximity to see if it can offer the capability. Examples include communicate data to the server, authorize going to lower power level, temperature reading, send an alert to local hub, send location data, triangulate location, any boxes in same group that already completed group objectives.

Nodes can be associated with items. Examples of an item includes, but are not limited to for example, a package, a box, pallet, a container, a truck or other conveyance, infrastructure such as a door, a conveyor belt, a light switch, a road, or any other thing that can be tracked, monitored, sensed, etc. or that can transmit data concerning its state or environment. In some examples, a server or a master node may associate the unique node identifiers with the items.

Communication paths between tape and/or non-tape nodes may be represented by a graph of edges between the corresponding assets (e.g., a storage unit, truck, or hub). In some embodiments, each node in the graph has a unique identifier. A set of connected edges between nodes is represented by a sequence of the node identifiers that defines a communication path between a set of nodes.

Figure 10A:
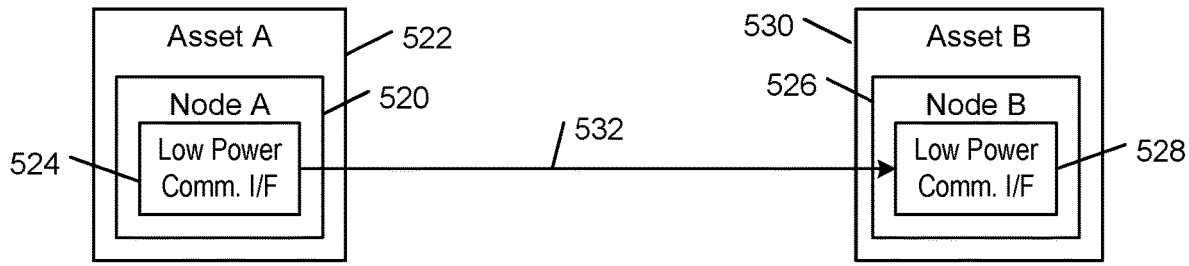
FIGS. 10A-10E are diagrammatic views of exemplary use cases for a distributed agent operating system, according to some embodiments.

Referring to FIG. 10A, a node 520 (Node A) is associated with an asset 522 (Asset A). In some embodiments, the node 520 may be implemented as a tape node that is used to seal the asset 522 or it may be implemented as a label node that is used to label the asset 522; alternatively, the node 520 may be implemented as a non-tape node that is inserted within the asset 522 or embedded in or otherwise attached to the interior or exterior of the asset 522. In the illustrated embodiment, the node 520 includes a low power communications interface 524 (e.g., a Bluetooth Low Energy communications interface). Another node 526 (Node B), which is associated with another asset 530 (Asset B), is similarly equipped with a compatible low power communications interface 528 (e.g., a Bluetooth Low Energy communications interface).

In an example scenario, in accordance with the programmatic code stored in its memory, node 526 (Node B) requires a connection to node 520 (Node A) to perform a task that involves checking the battery life of Node A. Initially, Node B is unconnected to any other nodes. In accordance with the programmatic code stored in its memory, Node B periodically broadcasts advertising packets into the surrounding area. When the other node 520 (Node A) is within range of Node B and is operating in a listening mode, Node A will extract the address of Node B and potentially other information (e.g., security information) from an advertising packet. If, according to its programmatic code, Node A determines that it is authorized to connect to Node B, Node A will attempt to pair with Node B. In this process, Node A and Node B determine each other's identities, capabilities, and services. For example, after successfully establishing a communication path 532 with Node A (e.g., a Bluetooth Low Energy formatted communication path), Node B determines Node A's identity information (e.g., master node), Node A's capabilities include reporting its current battery life, and Node A's services include transmitting its current battery life to other nodes. In response to a request from Node B, Node A transmits an indication of its current battery life to Node B.

Figure 10B:
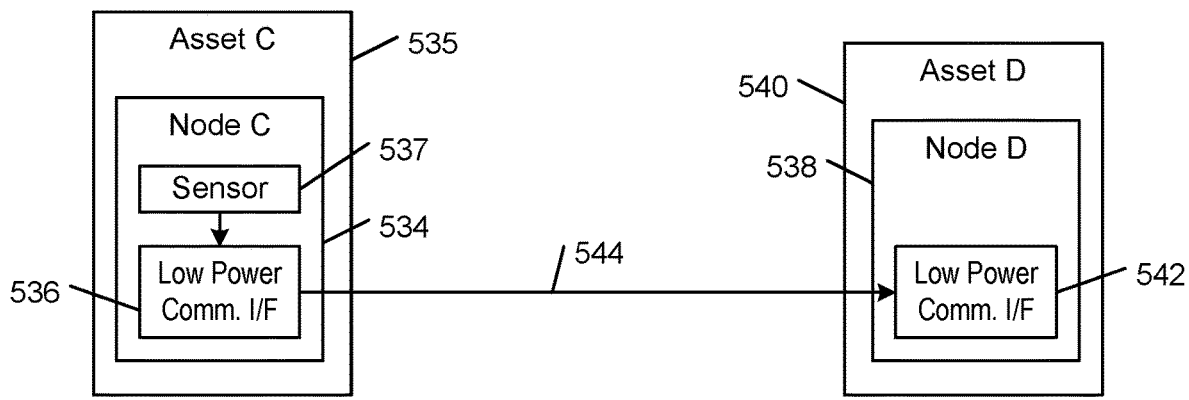

Referring to FIG. 10B, a node 534 (Node C) is associated with an asset 535 (Asset C). In the illustrated embodiment, the Node C includes a low power communications interface 536 (e.g., a Bluetooth Low Energy communications interface), and a sensor 537 (e.g., a temperature sensor). Another node 538 (Node D), which is associated with another asset 540 (Asset D), is similarly equipped with a compatible low power communications interface 542 (e.g., a Bluetooth Low Energy communications interface).

In an example scenario, in accordance with the programmatic code stored in its memory, Node D requires a connection to Node C to perform a task that involves checking the temperature in the vicinity of Node C. Initially, Node D is unconnected to any other nodes. In accordance with the programmatic code stored in its memory, Node D periodically broadcasts advertising packets in the surrounding area. When Node C is within range of Node D and is operating in a listening mode, Node C will extract the address of Node D and potentially other information (e.g., security information) from the advertising packet. If, according to its programmatic code, Node C determines that it is authorized to connect to Node D, Node C will attempt to pair with Node D. In this process, Node C and Node D determine each other's identities, capabilities, and services. For example, after successfully establishing a communication path 544 with Node C (e.g., a Bluetooth Low Energy formatted communication path), Node D determines Node C's identity information (e.g., a peripheral node), Node C's capabilities include retrieving temperature data, and Node C's services include transmitting temperature data to other nodes. In response to a request from Node D, Node C transmits its measured and/or locally processed temperature data to Node D.

Figure 10C:
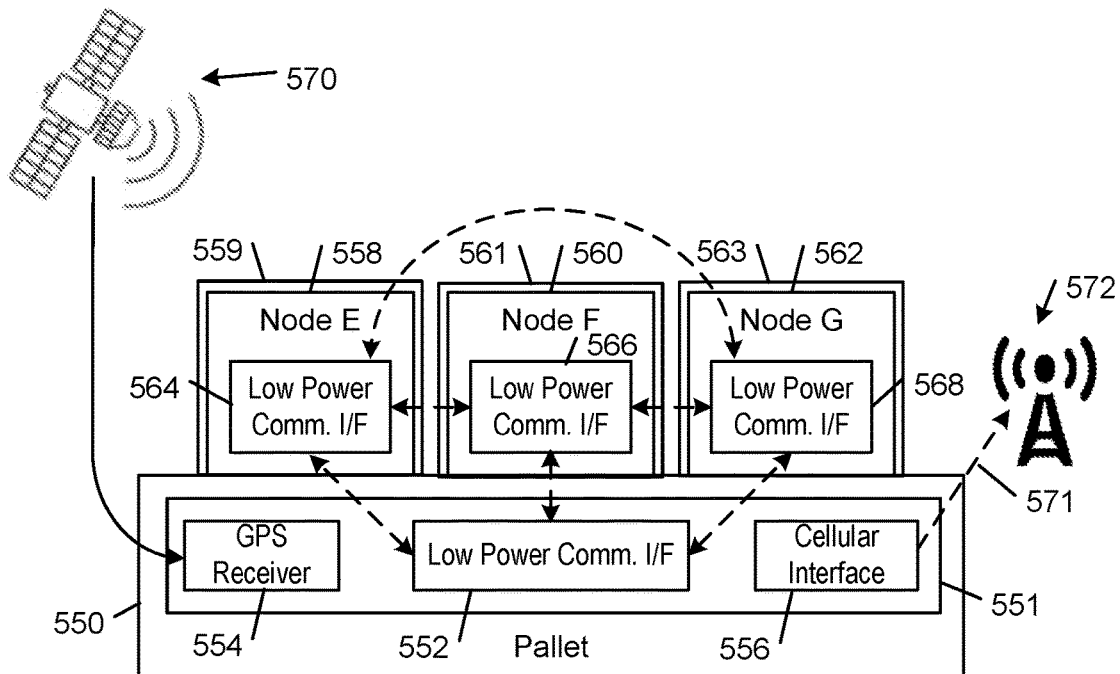

Referring to FIG. 10C, a pallet 550 is associated with a master node 551 that includes a low power communications interface 552, a GPS receiver 554, and a cellular communications interface 556. In some embodiments, the master node 551 may be implemented as a tape node or a label node that is adhered to the pallet 550. In other embodiments, the master node 551 may be implemented as a non-tape node that is inserted within the body of the pallet 550 or embedded in or otherwise attached to the interior or exterior of the pallet 550.

The pallet 550 provides a structure for grouping and containing assets 559, 561, 563 each of which is associated with a respective peripheral node 558, 560, 562 (Node E, Node F, and Node G). Each of the peripheral nodes 558, 560, 562 includes a respective low power communications interface 564, 566, 568 (e.g., Bluetooth Low Energy communications interface). In the illustrated embodiment, each of the nodes E, F, G and the master node 551 are connected to each of the other nodes over a respective low power communications path (shown by dashed lines).

In some embodiments, the assets 559, 561, 563 are grouped together because they are related. For example, the assets 559, 561, 563 may share the same shipping itinerary or a portion thereof. In an example scenario, the master pallet node 550 scans for advertising packets that are broadcasted from the peripheral nodes 558, 560, 562. In some examples, the peripheral nodes broadcast advertising packets during respective scheduled broadcast intervals. The master node 551 can determine the presence of the assets 559, 561, 563 in the vicinity of the pallet 550 based on receipt of one or more advertising packets from each of the nodes E, F, and G. In some embodiments, in response to receipt of advertising packets broadcasted by the peripheral nodes 558, 560, 562, the master node 551 transmits respective requests to the server to associate the master node 551 and the respective peripheral nodes 558, 560, 562. In some examples, the master tape node requests authorization from the server to associate the master tape node and the peripheral tape nodes. If the corresponding assets 559, 561, 563 are intended to be grouped together (e.g., they share the same itinerary or certain segments of the same itinerary), the server authorizes the master node 551 to associate the peripheral nodes 558, 560, 562 with one another as a grouped set of assets. In some embodiments, the server registers the master node and peripheral tape node identifiers with a group identifier. The server also may associate each node ID with a respective physical label ID that is affixed to the respective asset.

In some embodiments, after an initial set of assets is assigned to a multi-asset group, the master node 551 may identify another asset arrives in the vicinity of the multi-asset group. The master node may request authorization from the server to associate the other asset with the existing multi-asset group. If the server determines that the other asset is intended to ship with the multi-asset group, the server instructs the master node to merge one or more other assets with currently grouped set of assets. After all assets are grouped together, the server authorizes the multi-asset group to ship. In some embodiments, this process may involve releasing the multi-asset group from a containment area (e.g., customs holding area) in a shipment facility.

In some embodiments, the peripheral nodes 558, 560, 562 include environmental sensors for obtaining information regarding environmental conditions in the vicinity of the associated assets 559, 561, 563. Examples of such environmental sensors include temperature sensors, humidity sensors, acceleration sensors, vibration sensors, shock sensors, pressure sensors, altitude sensors, light sensors, and orientation sensors.

In the illustrated embodiment, the master node 551 can determine its own location based on geolocation data transmitted by a satellite-based radio navigation system 570 (e.g., GPS, GLONASS, and NAVSTAR) and received by the GPS receiver 554 component of the master node 551. In an alternative embodiment, the location of the master pallet node 551 can be determined using cellular based navigation techniques that use mobile communication technologies (e.g., GSM, GPRS, CDMA, etc.) to implement one or more cell-based localization techniques. After the master node 551 has ascertained its location, the distance of each of the assets 559, 561, 563 from the master node 551 can be estimated based on the average signal strength of the advertising packets that the master node 551 receives from the respective peripheral node. The master node 551 can then transmit its own location and the locations of the asset nodes E, F, and G to a server over a cellular interface connection with a cell tower 572. Other methods of determining the distance of each of the assets 559, 561, 563 from the master node 551, such as Received Signal-Strength Index (RSSI) based indoor localization techniques, also may be used.

In some embodiments, after determining its own location and the locations of the peripheral nodes, the master node 551 reports the location data and the collected and optionally processed (e.g., either by the peripheral nodes peripheral nodes 558, 560, 562 or the master node 551) sensor data to a server over a cellular communication path 571 on a cellular network 572.

In some examples, nodes are able to autonomously detect logistics execution errors if assets that suppose to travel together no longer travel together, and raise an alert. For example, a node (e.g., the master node 551 or one of the peripheral nodes 558, 560, 562) alerts the server when the node determines that a particular asset 559 is being or has already been improperly separated from the group of assets. The node may determine that there has been an improper separation of the particular asset 559 in a variety of ways. For example, the associated node 558 that is bound to the particular asset 559 may include an accelerometer that generates a signal in response to movement of the asset from the pallet. In accordance with its intelligent agent program code, the associated node 558 determines that the master node 551 has not disassociated the particular asset 559 from the group and therefore broadcasts advertising packets to the master node, which causes the master node 551 to monitor the average signal strength of the advertising packets and, if the master node 551 determines that the signal strength is decreasing over time, the master node 551 will issue an alert either locally (e.g., through a speaker component of the master node 551) or to the server.

Figure 10D:
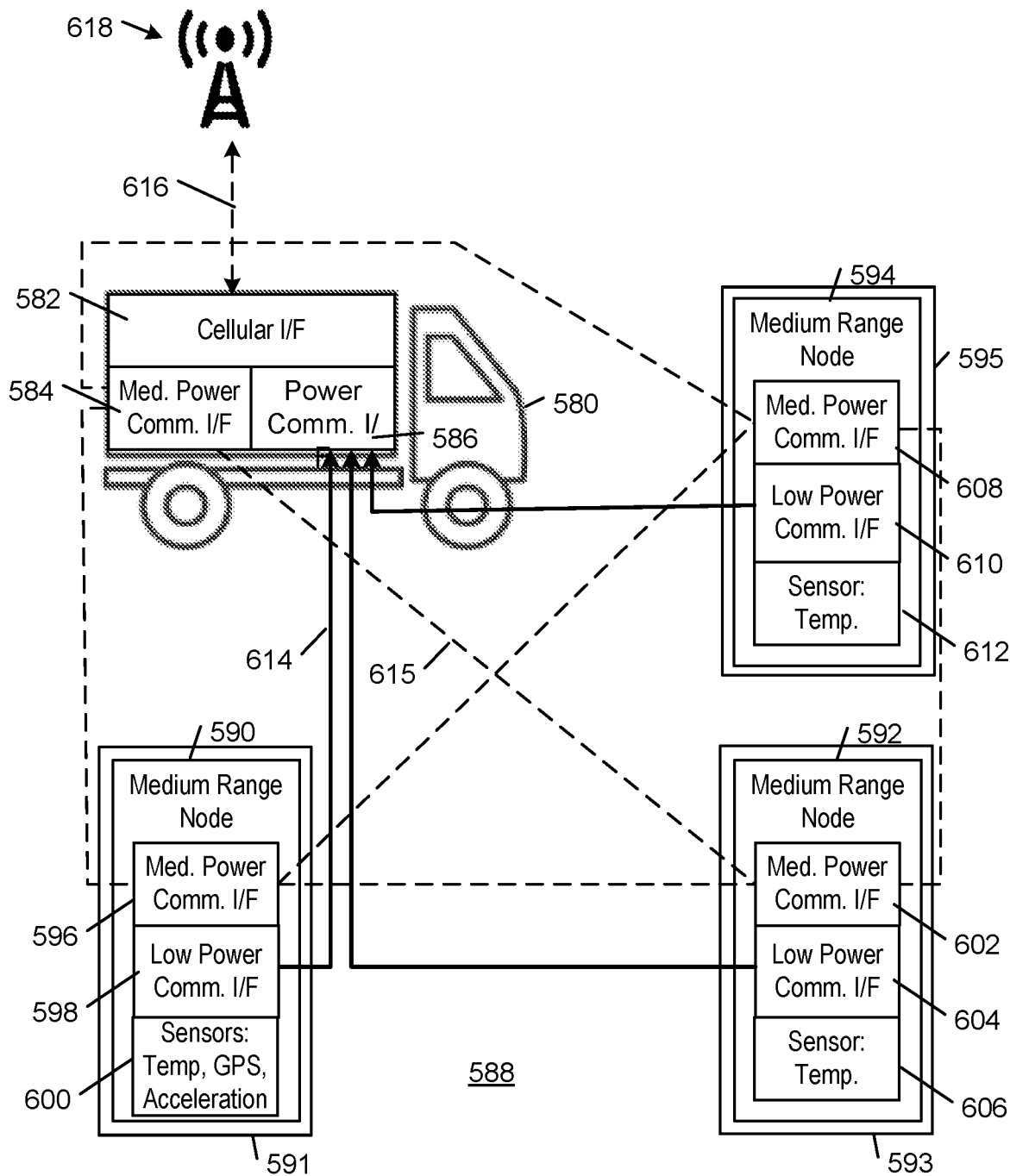

Referring to FIG. 10D, a truck 580 is configured as a mobile node or mobile hub that includes a cellular communications interface 582, a medium power communications interface 584, and a low power communications interface 586. The communications interfaces 580-586 may be implemented on one or more tape and non-tape nodes. In an illustrative scenario, the truck 580 visits a storage facility, such as a warehouse 588, to wirelessly obtain temperature data generated by temperature sensors in the medium range nodes 590, 592, 594. The warehouse 588 contains nodes 590, 592, and 594 that are associated with respective assets 591, 593, 595. In the illustrated embodiment, each node 590-594 is a medium range node that includes a respective medium power communications interface 596, 602, 608, a respective low power communications interface 598, 604, 610 and one or more respective sensors 600, 606, 612. In the illustrated embodiment, each of the asset nodes 590, 592, 594 and the truck 580 is connected to each of the other ones of the asset nodes through a respective medium power communications path (shown by dashed lines). In some embodiments, the medium power communications paths are LoRa formatted communication paths.

In some embodiments, the communications interfaces 584 and 586 (e.g., a LoRa communications interface and a Bluetooth Low Energy communications interface) on the node on the truck 580 is programmed to broadcast advertisement packets to establish connections with other network nodes within range of the truck node. A warehouse 588 includes medium range nodes 590, 592, 594 that are associated with respective containers 591, 593, 595 (e.g., assets, boxes, pallets, and the like). When the truck node's low power interface 586 is within range of any of the medium range nodes 590, 592, 594 and one or more of the medium range nodes is operating in a listening mode, the medium range node will extract the address of truck node and potentially other information (e.g., security information) from the advertising packet. If, according to its programmatic code, the truck node determines that it is authorized to connect to one of the medium range nodes 590, 592, 594, the truck node will attempt to pair with the medium range node. In this process, the truck node and the medium range node determine each other's identities, capabilities, and services. For example, after successfully establishing a communication path with the truck node (e.g., a Bluetooth Low Energy formatted communication path 614 or a LoRa formatted communication path 617), the truck node determines the identity information for the medium range node 590 (e.g., a peripheral node), the medium range node's capabilities include retrieving temperature data, and the medium range node's services include transmitting temperature data to other nodes. Depending of the size of the warehouse 588, the truck 580 initially may communicate with the nodes 590, 592, 594 using a low power communications interface (e.g., Bluetooth Low Energy interface). If any of the anticipated nodes fails to respond to repeated broadcasts of advertising packets by the truck 580, the truck 580 will try to communicate with the non-responsive nodes using a medium power communications interface (e.g., LoRa interface). In response to a request from the truck node 584, the medium range node 590 transmits an indication of its measured temperature data to the truck node. The truck node repeats the process for each of the other medium range nodes 592, 594 that generate temperature measurement data in the warehouse 588. The truck node reports the collected (and optionally processed, either by the medium range nodes 590, 592, 594 or the truck node) temperature data to a server over a cellular communication path 616 with a cellular network 618.

Figure 10E:
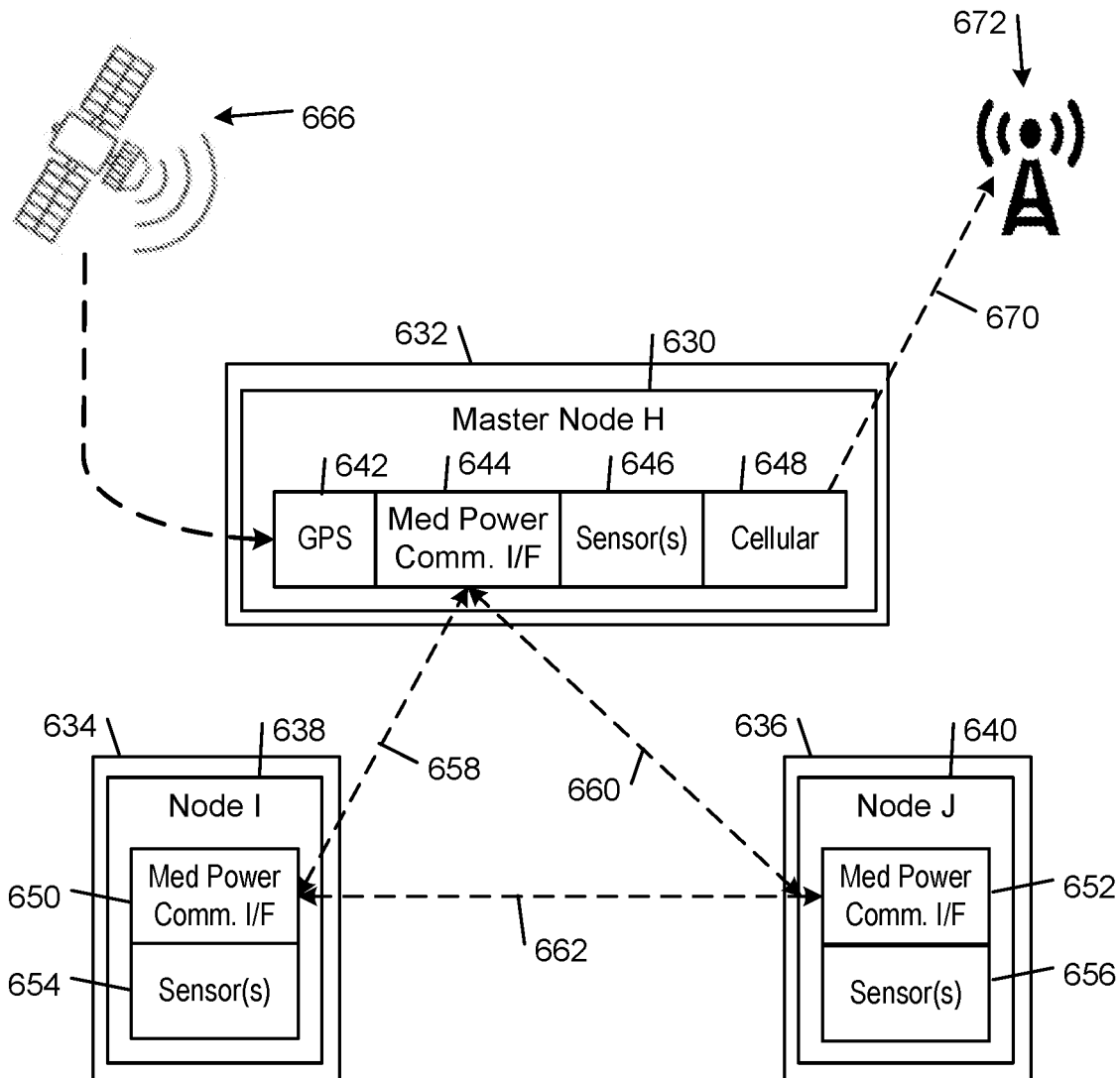

Referring to FIG. 10E, a master node 630 is associated with an item 632 (e.g., an asset) and grouped together with other items 634, 636 (e.g., assets) that are associated with respective peripheral nodes 638, 640. The master node 630 includes a GPS receiver 642, a medium power communications interface 644, one or more sensors 646, and a cellular communications interface 648. Each of the peripheral nodes 638, 640 includes a respective medium power communications interface 650, 652 and one or more respective sensors 654, 656. In the illustrated embodiment, the peripheral and master nodes are connected to one another other over respective pairwise communications paths (shown by dashed lines). In some embodiments, the nodes 630 638, 640 communicate through respective LoRa communications interfaces over LoRa formatted communications paths 658, 660, 662.

In the illustrated embodiment, the master and peripheral nodes 638, 638, 640 include environmental sensors for obtaining information regarding environmental conditions in the vicinity of the associated assets 632, 634, 636. Examples of such environmental sensors include temperature sensors, humidity sensors, acceleration sensors, vibration sensors, shock sensors, pressure sensors, altitude sensors, light sensors, and orientation sensors.

In accordance with the programmatic code stored in its memory, the master node 630 periodically broadcasts advertising packets in the surrounding area. When the peripheral nodes 638, 640 are within range of master node 630, and are operating in a listening mode, the peripheral nodes 638, 640 will extract the address of master node 630 and potentially other information (e.g., security information) from the advertising packets. If, according to their respective programmatic code, the peripheral nodes 638, 640 determine that hey are authorized to connect to the master node 630, the peripheral nodes 638, 640 will attempt to pair with the master node 630. In this process, the peripheral nodes 638, 640 and the master node and the peripheral nodes determine each other's identities, capabilities, and services. For example, after successfully establishing a respective communication path 658, 660 with each of the peripheral nodes 638, 640 (e.g., a LoRa formatted communication path), the master node 630 determines certain information about the peripheral nodes 638, 640, such as their identity information (e.g., peripheral nodes), their capabilities (e.g., measuring temperature data), and their services include transmitting temperature data to other nodes.

After establishing LoRa formatted communications paths 658, 660 with the peripheral nodes 638, 640, the master node 630 transmits requests for the peripheral nodes 638, 640 to transmit their measured and/or locally processed temperature data to the master node 630.

In the illustrated embodiment, the master node 630 can determine its own location based on geolocation data transmitted by a satellite-based radio navigation system 666 (e.g., GPS, GLONASS, and NAVSTAR) and received by the GPS receiver 642 component of the master node 630. In an alternative embodiment, the location of the master node 630 can be determined using cellular based navigation techniques that use mobile communication technologies (e.g., GSM, GPRS, CDMA, etc.) to implement one or more cell-based localization techniques. After the master node 630 has ascertained its location, the distance of each of the assets 634, 636 from the master node 630 can be estimated based on the average signal strength of the advertising packets that the master node 630 receives from the respective peripheral node. The master node 630 can then transmit its own location and the locations of the asset nodes E, F, and G to a server over a cellular interface connection with a cell tower 672. Other methods of determining the distance of each of the assets 634, 636 from the master node 630, such as Received Signal-Strength Index (RSSI) based indoor localization techniques, also may be used.

In some embodiments, after determining its own location and the locations of the peripheral nodes, the master node 630 reports the location data the collected and optionally processed (e.g., either by the peripheral nodes peripheral nodes 634, 636 or the master node 630) sensor data to a server over a cellular communication path 670 on a cellular network 672.

Dynamic Form Factors to Determine Direction of Movement

In fast-paced environments such as hospitals, assets may be moved frequently throughout buildings, wards, or other sections of an area. It is valuable to track assets as movement occurs in order to ensure that assets are accounted for, e.g., are not lost or misrepresented as being in or out of use. However, because assets may be moved quickly and unpredictably, there are difficulties in optimizing power usage and accurate data collection for asset tracking.

The wireless tracking system 400 monitors heartbeat signals to monitor locations and usage information for assets. Heartbeat signals are low-power signals transmitted periodically by tracking devices of the wireless sensing system associated with assets, e.g., tape nodes adhered or affixed to machines or items. The tracking device is is a tape node, according to some embodiments. Heartbeat signals are signals transmitted periodically by tracking devices or nodes of the wireless sensing system associated with assets, e.g., tape nodes adhered or affixed to machines or items. The heartbeat signals allow for the monitoring of the assets, while minimizing the power consumption of the tracking devices. For example, the heartbeat signal may include a lower volume of data than other signals transmitted by the tracking device. Heartbeat signals may be transmitted using low-range wireless communication protocols and system (e.g., Bluetooth or BLE). For most applications and situations, heartbeat signals are transmitted infrequently, e.g., once a day, once an hour. The detection of a heartbeat signal by a wireless node associated with a known location, such as a gateway node, is used by the tracking system 400 to determine that the wireless node is in a vicinity of the known location, according to some embodiments. However, in fast-paced environments such as hospitals, it is possible for assets to be moved too quickly for heartbeat signals to provide useful information. For example, an asset such as a bed loaded onto an ambulance may be moved too quickly for the wireless sensing system to accurately receive data corresponding to the movement. While increasing the frequency of the heartbeat signals, e.g., a heartbeat per second, may accommodate fast-moving assets, high frequency heartbeats drains battery life of tape nodes.

According to some embodiments, a heartbeat signal of a wireless node is a minimal data signal that the node transmits to indicate to the IOT system 400 that the node is functioning correctly. In some cases, the heartbeat signal also indicates that the node has not detected any anomalous events or conditions for an asset associated with the node. The heartbeat signal may be transmitted as a data packet that has a minimal size, which allows the node to check in with the IOT system 400 without unnecessarily consuming resources of the node and the IOT system, such as energy reserved in a battery of the node. The heartbeat signal may include an identifier associated with the node (e.g., a unique identifier, a hardware identifier, a MAC address, a software identifier, or some other identifier). The heartbeat signal may also include a flag which indicates a good or normal status of the node and optionally an associated asset. The node may transmit the heartbeat signal with a relatively low frequency, according to some embodiments. For example, the node may transmit the heartbeat signal to another node of the IOT system 400 once every hour or once every day. The IOT system 400 may be configured to detect that a status of a node is not normal, if the heartbeat signal is not received during a period of time. For example, if the IOT system 400 has not received a heartbeat signal from a node for a period of over 24 hours, the IOT system 400 may determine that the node is not functioning properly.

In an embodiment, a wireless sensing system deploys one or more sets of gateway nodes through a building or area of interest to detect assets moving through gates. Gates may be, for example, doorways, hallways, or other threshold areas. In an embodiment, a direction of movement through a gate may be used by the wireless sensing system to approximate a likely location for the asset. For example, an asset moving through an external loading door of a hospital is tagged by the wireless sensing system as most likely being loaded onto an ambulance. The one or more sets of gateway nodes are configured to receive heartbeat signals from tape nodes associated with assets and to determine, based on the respective signal strengths of the heartbeat signals, a direction of movement for assets. In some embodiments, the one or more sets of gateway nodes are deployed in locations throughout a building or area of interest based on structural thresholds. For example, a first node of a set of gateway nodes is deployed inside of a room and a second node of the set of gateway nodes is deployed in a hallway outside of the room, enabling the wireless sensing system to ensure that an asset is accurately tracked as passing through the door. In some examples, a node of a set of gateway nodes deployed inside of a room is further configured to conduct a check for an asset being within a room to confirm that the asset has moved through a doorway threshold.

In an embodiment, the wireless sensing system trains and applies a machine learned model. The machine learned model is trained to receive as input one or more signals associated with one or more signal strengths and to output a most likely direction of movement for an asset. For example, the machine learned model outputs a label identifying a direction (e.g., north, south, west, east), a name of a corresponding location (e.g., ambulance loading area, storage room, etc.), or the like. Aspects of the machine learned model may be stored on one or more tape nodes, one or more client devices, one or more gateway nodes, one or more other nodes of the wireless sensing system, a cloud or server of the wireless sensing system, or some combination thereof. In some embodiments, a set of gateway nodes locally applies the machine learned model trained to output a most likely direction of movement for an asset. In another example, aspects of the machine learned model are distributed across a plurality of nodes of the wireless sensing system, and the machine learned model is applied by communicating between nodes of the wireless sensing system.

To ensure that a tape node associated with a moving asset transmits heartbeat signals at appropriate intervals to optimize battery life and to provide adequate information for signal strength computations, the wireless sensing system transmits instructions to tape nodes to identify certain contexts or locations in which a higher frequency heartbeat signal is required. Because shorter range communications are more battery-efficient than longer range communications, it is beneficial for tape nodes to communicate heartbeat signals to gateway nodes when in short range. In an embodiment, gateway nodes are deployed as leading indicators through a building or area of interest to provide instructions to tape nodes to increase a heartbeat signal frequency upon approaching a gate. For example, a gateway node is located at an entrance of a loading zone and instructs tape nodes within the loading zone to increase a frequency of heartbeat signal as the tape nodes move towards a threshold door. In another example, one or more gateway nodes are located at conveyer belts and are configured to instruct tape nodes on the conveyer belt to increase a frequency of heartbeat signals within a threshold amount of time (e.g., increase heartbeat signal in 5 minutes).

In other embodiments, the gateway node may provide other or additional instructions to a tape node. For example, the gateway node may additionally instruct a tape node to increase or decrease an amount of sensor data collection, to increase or decrease an amount of data transmittal, to modify a means or channel for communication, to establish or disconnect to another entity of the wireless sensing system, and the like. In another example, the gateway node may instruct a tape node to decrease or reduce a frequency of heartbeat pings or other communications, e.g., at the threshold to a long-term storage room in which it is unlikely to be moved and, as such, can reduce communications to preserve battery life.

Figure 11A:
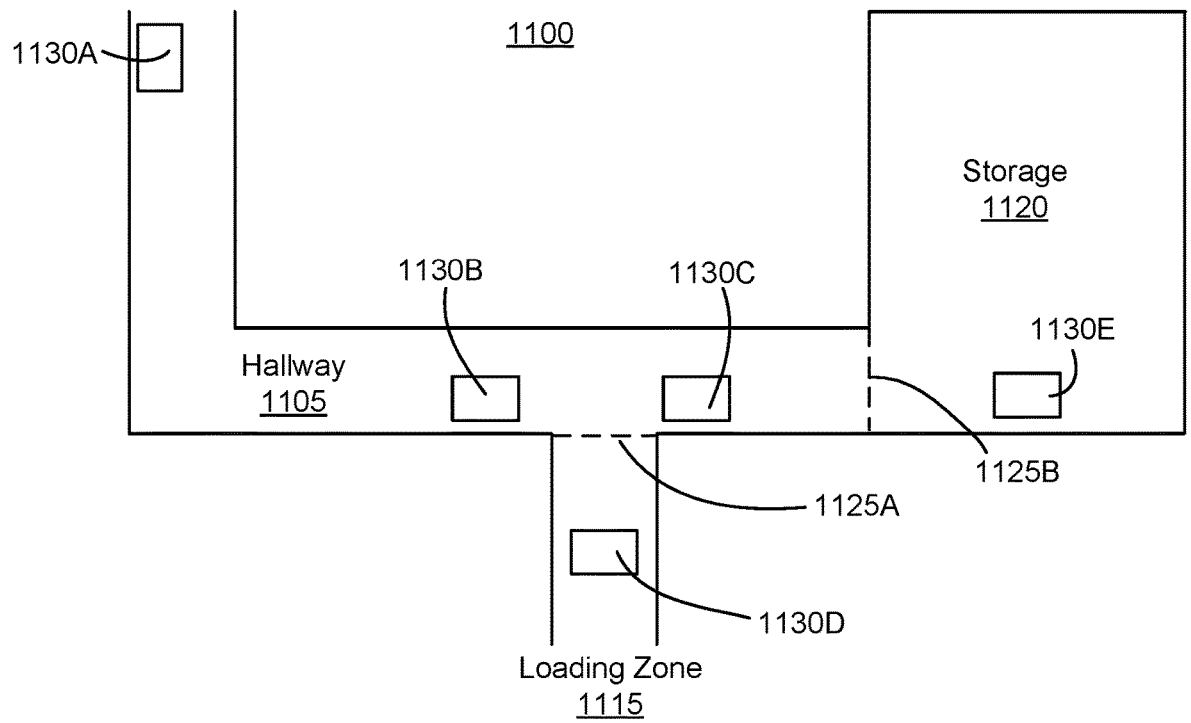
FIG. 11A is an example environment comprising a wireless sensing system having a plurality of gateway nodes configured to determine direction of movement for assets through gates.

FIG. 11A is an example environment 1100 comprising a wireless sensing system having a plurality of gateway nodes 1130 configured to determine direction of movement for assets through gates, according to some embodiments. A hallway 1105 comprises of a first gate 1125A between the hallway and a loading zone 1115 and a second gate 1125B between the hallway and a storage area 1120. A first gateway node 1130A is deployed to act as a leading indicator, such that tape nodes within a range of the first gateway node receive an instruction to increase a frequency of a heartbeat signal. A second set of gateway nodes 1130B, 1130C, 1130D are configured to determine whether a tape node associated with a moving asset moves through the first gate 1125A into the loading zone 1115 or passes by the first gate towards the second gate 1125B to the storage 1120. The second set of gateway nodes may use received signal strength (e.g., RSSI) of wireless signals received from a tape node on an asset to determine the location and movement of the asset through the environment 1100. Similarly, a tape node on an asset may use received signal strength of wireless signals from the gateway nodes to determine a relative location of the asset with respect to the gateway nodes. The gateway nodes each have a known location which is stored on the gateway node and also on a database of the tracking system 400. Thus, one or more gateway nodes can be used to triangulate the position of a tape node on an asset in the environment 1100 or determine a distance from a gateway node's location. The triangulation or distance measurement can be used to determine a trajectory through a space, especially a confined space such as the hallway 1105, including a direction of movement.

Figure 11B:
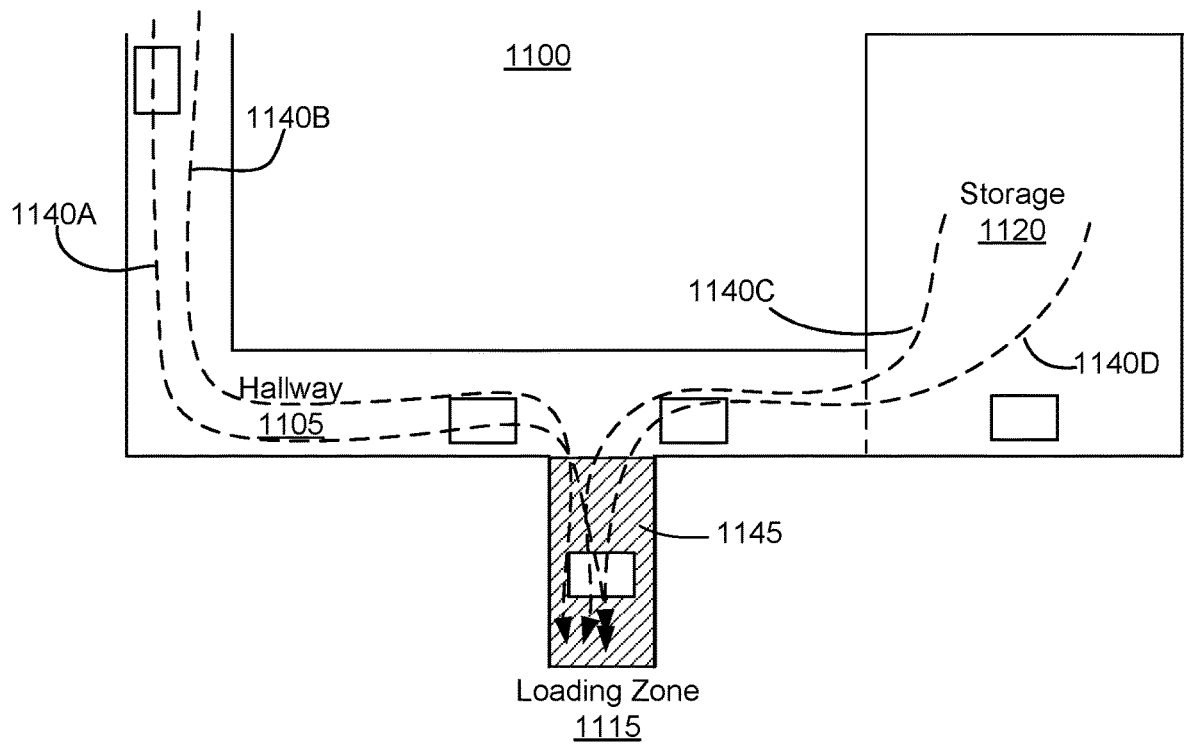
FIG. 11B shows the paths of a plurality of mobile assets moving through the example environment shown in FIG. 11A, according to some embodiments.

FIG. 11B shows the paths of a plurality of mobile assets moving through the example environment 1100 shown in FIG. 11A, according to some embodiments. The wireless sensing system identifies a plurality of paths 1140A-D corresponding to a plurality of mobile assets in the environment 1100. Based on the plurality of paths 1140, the wireless sensing system identifies a strategically important zone 1145 corresponding to the loading zone 1115. In other embodiments, the strategically important zone 1145 is predetermined. For example, the strategically important zone 1145 may correspond to a gate, an entranceway, an exit, a checkpoint, or some other area. If the strategically important zone 1145 is an exit, for example, it may be valuable to have increased accuracy in tracking the flow of assets through the strategically important zone to determine if assets have left the environment 1100. In an embodiment, the strategically important zone 1145 is delineated by geofences surrounding the strategically important zone. In an embodiment, the wireless sensing system identifies the strategically important zone 1145 using one or more clustering algorithms to the plurality of paths 1140. The clustering algorithms identify a common zone or zone capturing more than a threshold number of paths 1140. For example, the wireless sensing system identifies a strategically important zone 1145 as a loading/unloading zone in a storage facility based on a plurality of paths 1140 entering and exiting the storage facility through the strategically important zone, e.g., a plurality of paths begin and end communications with the wireless sensing system while moving in or through the loading/unloading zone. In other examples, strategically important zones 1145 may include storage areas wherein large numbers of assets are held, refrigeration units for cold chain assets, or areas of a facility wherein assets are processed, inspected, or otherwise altered in some way.

Responsive to the strategically important zone 1145 being identified, the wireless sensing system may transmit an instruction to tape nodes associated with mobile assets to modify one or more operations when the tape nodes approach, enter, leave, or otherwise interact with the strategically important zone or geofences corresponding to the strategically important zone. For example, the instructions to modify one or more operations may include one or more of: an instruction to enter a gate detection mode; an instruction to increase a frequency of communication; an instruction to decrease a frequency of communication; an instruction to enter a hibernation mode; an instruction to activate a particular form of communication. In the example of FIG. 11B, because a loading zone 1115 corresponds to a need for higher frequency communications due to assets moving quickly, the wireless sensing system detecting an mobile asset moving into strategically important zone 1145 transmits an instruction to a corresponding tape node to increase the communication frequency.

In an embodiment, a wireless sensing system deploys one or more sets of gateway nodes through a building or area of interest to detect assets moving through gates, into or through areas, or past areas. The gateway nodes may be a wireless communication device incorporated into the infrastructure of a room, building, or an area, according to some embodiments. For example, the gateway node may be a wireless communication device that can be plugged into a power outlet. In other embodiments, the gateway node is an adhesive tape node that is installed on a portion of a room, building, or an area. The gateway node may be an adhesive tape node that has a longer communication range (e.g., a tape node including a LoRa, cellular, or satellite communication system) than a tape node installed on an asset for tracking the asset. Gates may be, for example, doorways, hallways, or other threshold areas. The gateway nodes may also be installed in areas other than a gate, such as a wall of a room. In an embodiment, a direction of movement through a gate may be used by the wireless sensing system to approximate a likely location for the asset. For example, an asset moving through an external loading door of a hospital is tagged by the wireless sensing system as most likely being loaded onto an ambulance. The one or more sets of gateway nodes are configured to receive heartbeat signals from tape nodes associated with assets and to determine, based on the respective signal strengths of the heartbeat signals, a direction of movement for assets.

In some embodiments, the one or more sets of gateway nodes are deployed in locations throughout a building or area of interest based on structural thresholds. For example, a first node of a set of gateway nodes is deployed on a front wall of a room and a second node of the set of gateway nodes is deployed on a back wall of the room, enabling the wireless sensing system to ensure that an asset is accurately tracked as passing through the door. The wireless sensing system determines based on relative signal strengths of communications received by the first node and the second node whether tape nodes associated with mobile assets have entered, moved through, or passed the room. In some examples, a node of a set of gateway nodes deployed inside of a room is further configured to conduct a check for an asset being within a room to confirm that the asset has moved through a doorway threshold.

In other embodiments, the one or more sets of gateway nodes are deployed in locations that correspond to boundaries of an area that are not defined by a structural threshold or component. For example, an area of interest may be a section of a room, hallway, outdoor area, or other area. A tape node may be installed on one or more objects or portions of the area that corresponds to a border or boundary of the area. The wireless sensing system may thus, track the movement of assets through the area, as described herein.

In an embodiment, the wireless sensing system trains and applies a machine learning model. The machine learning model is trained to receive as input one or more signals relevant to tracked locations of assets and to output a most likely direction of movement for the assets. The one or more signals may be, for example, one or more measurements of signal strength between nodes associated with assets and gateway nodes (e.g., RSSI signals from the gateway nodes), GPS or other location data associated with gateway nodes or nodes associated with assets, and the like. For example, the machine learning model generates a label identifying a direction (e.g., north, south, west, east), a name of a corresponding location (e.g., ambulance loading area, storage room, etc.), or the like based on one or more input signals that are relevant to the tracked location of the asset. In other examples, the trained machine learning model generates a prediction of whether the asset is in an area of interest (e.g., a room) based on one or more input signals that are relevant to the tracked location of the asset. In other examples, the trained machine learning model generates a prediction of whether the asset has entered, exited, or passed by an area of interest (e.g., a room) based on one or more input signals that are relevant to the tracked location of the asset.

In an embodiment, the wireless sensing system applies one or more clustering algorithms to data gathered describing movement of a plurality of assets through a building or other area of interest to determine strategically important zones. Strategically important zones may be, for example, areas wherein assets are likely to experience particular events (e.g., unloading or loading zones), areas wherein tape nodes associated with assets should enter a specific mode or initiate a specific mode of communication, and the like. In some embodiments, strategically important zones are delineated by geofences surrounding the strategically important zones. The wireless sensing system may determine appropriate geofences based on the clustering algorithms (e.g., automatically determining an appropriate size and shape of the strategically important zone based on historic movement of assets through or around the strategically important zone) or may request information describing strategically important zones from users of the wireless sensing system.

Responsive to identifying a strategically important zone, the wireless sensing system may transmit instructions to tape nodes based at least in part on proximity of the tape nodes to strategically important zones. For example, the wireless sensing system transmits instructions to tape nodes to identify certain contexts or locations in which a higher frequency heartbeat signal is required in order to optimize battery life while ensuring that adequate information is provided for each tape node. Because shorter range communications are more battery-efficient than longer range communications, it is beneficial for tape nodes to communicate heartbeat signals to gateway nodes when in short range. In an embodiment, gateway nodes are deployed to transmit leading indicator signals to tape nodes, gateway nodes, client devices, and/or other nodes of the system located throughout a building or area of interest or around a strategically important zone. In response to receiving the leading indicator signal, the tape nodes increase a frequency of transmission for a heartbeat signal corresponding to the tape nodes approaching a gate or strategically important zone. For example, a gateway node is located at an entrance of a loading zone and transmits the leading indicator signal to tape nodes within the loading zone. The tape nodes increase a frequency of heartbeat signal as the tape nodes move towards a threshold door, in response. In another example, one or more gateway nodes are located at conveyer belts and are configured to instruct tape nodes on the conveyer belt to increase a frequency of heartbeat signals within a threshold amount of time (e.g., increase heartbeat signal in 5 minutes).

In other embodiments, the gateway node may provide other or additional instructions to a tape node responsive to the tape node approaching or leaving a strategically important zone. For example, the gateway node may additionally instruct a tape node to increase or decrease an amount of sensor data collection, to increase or decrease an amount of data transmittal, to modify a means or channel for communication, to establish or disconnect to another entity of the wireless sensing system, and the like. In another example, the gateway node may instruct a tape node to decrease or reduce a frequency of heartbeat pings or other communications, e.g., at the threshold to a long-term storage room in which it is unlikely to be moved and, as such, can reduce communications to preserve battery life.

Figure 12:
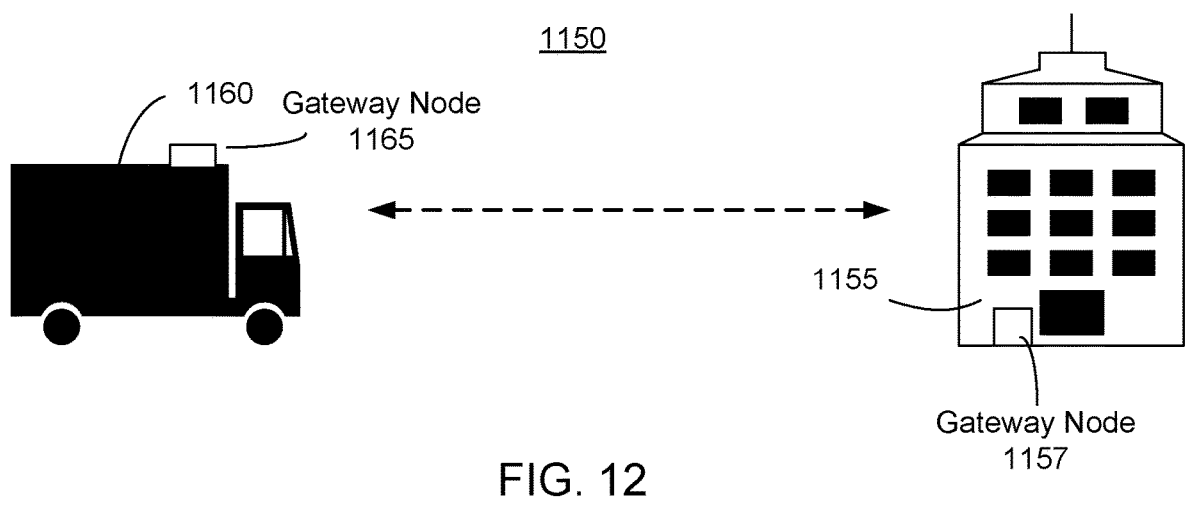
FIG. 12 is an example environment comprising a wireless sensing system having a gateway node associated with a vehicle, according to some embodiments.

FIG. 12 is an example environment 1150 comprising a wireless sensing system having a gateway node 1165 associated with a vehicle 1160, according to some embodiments. The gateway node 1165 is configured to communicate with one or more tape nodes inside the vehicle. The tape nodes inside the vehicle 1160 may each be associated with one or more assets or persons being transported by the vehicle 1160. In an embodiment, the gateway node 1165 is configured to communicate with one or more nodes, e.g., gateway node 1157, associated with a destination building 1155. The gateway node 1157 may do so using short range (e.g., Bluetooth), medium range wireless communications (e.g., LoRa or LoRaWAN), or Long-range wireless communications (e.g., cellular, satellite, or an internet connection) to directly or indirectly communicate with the one or more nodes in the destination building 1155. For example, the vehicle 1160 is an ambulance and the destination building 1155 is a hospital. Responsive to the gateway node 1165 of the vehicle 1160 determining that it is within a threshold distance of the destination building 1155, the gateway node instructs one or more tape nodes within the vehicle 1160 to begin transmitting heartbeat signals or other wireless communications at an increased frequency, such that the one or more tape nodes within the vehicle 1160 are transmitting at high frequency when entering the destination building 1155 or another environment requiring high frequency heartbeat signals.

The gateway node 1165 may determine that the vehicle 1160 is within the threshold distance of the destination building 1160 based on wireless communications received from the gateway 1157. For example, the threshold distance may correspond to a wireless communication range for a wireless communication protocol or system used to communicate between the gateway node 1165 and the gateway node 1157. When a wireless communication connection is established between the gateway nodes 1165, 1167, the gateway node 1165 determines that it is within the threshold distance. The distance between the vehicle 1160 and the destination building may be determined using other methods, such as by GPS locationing.

While the destination 1155 in the example of FIG. 12 is a building, the embodiments disclosed herein are not limited thereto, and the destination 1155 may be an outdoor environment, and indoor environment, or some other type of environment.

Figure 13:
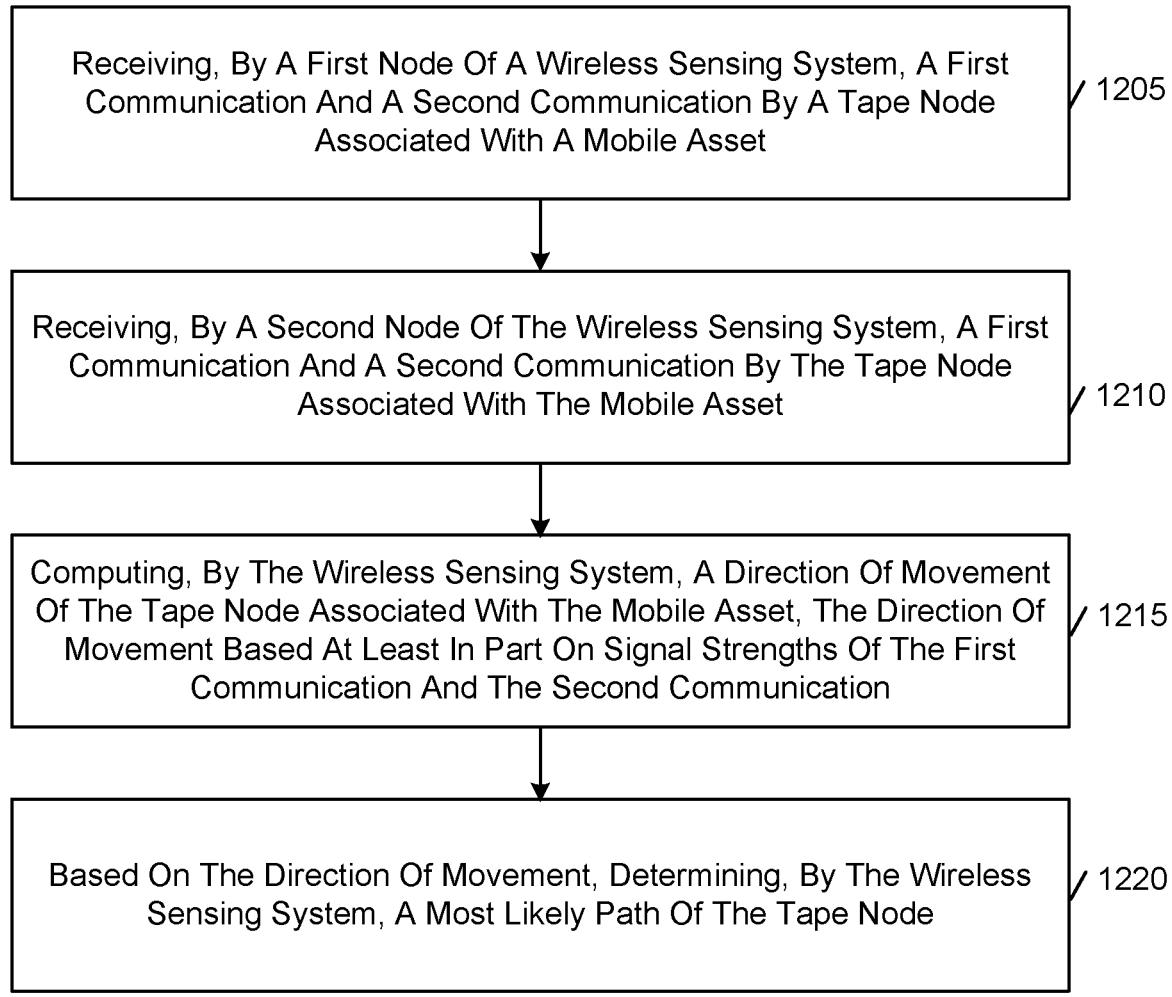
FIG. 13 is a flow diagram for a method for determining direction of movement of assets through gates, according to some embodiments.

FIG. 13 is a flow diagram for a method for determining direction of movement of assets through gates, according to some embodiments. A first node of a wireless sensing system receives a first communication and a second communication by a tape node associated with a mobile asset (FIG. 13, block 1205). The first communication and the second communication are associated with respective signal strengths and respective timestamps. A second node of the wireless sensing system receives a first communication and a second communication by the tape node associated with the mobile asset, associated with respective signal strengths and timestamps (FIG. 13, block 1210). The first and second nodes of the wireless sensing system are associated with location information (e.g., are stationary gateway nodes deployed in a building or area of interest). The wireless sensing system computes a direction of movement of the tape node associated with the mobile asset based at least in part on the respective signal strengths of the first and second communications (FIG. 13, block 1215). Based on the direction of movement, the wireless sensing system determines a most likely path of the tape node (FIG. 13, block 1220).

In other embodiments, the method may include additional, fewer, or different steps, and the steps may be performed in a different order. In other embodiments, steps of the method may be performed by different components of the sensing system.

Figure 14:
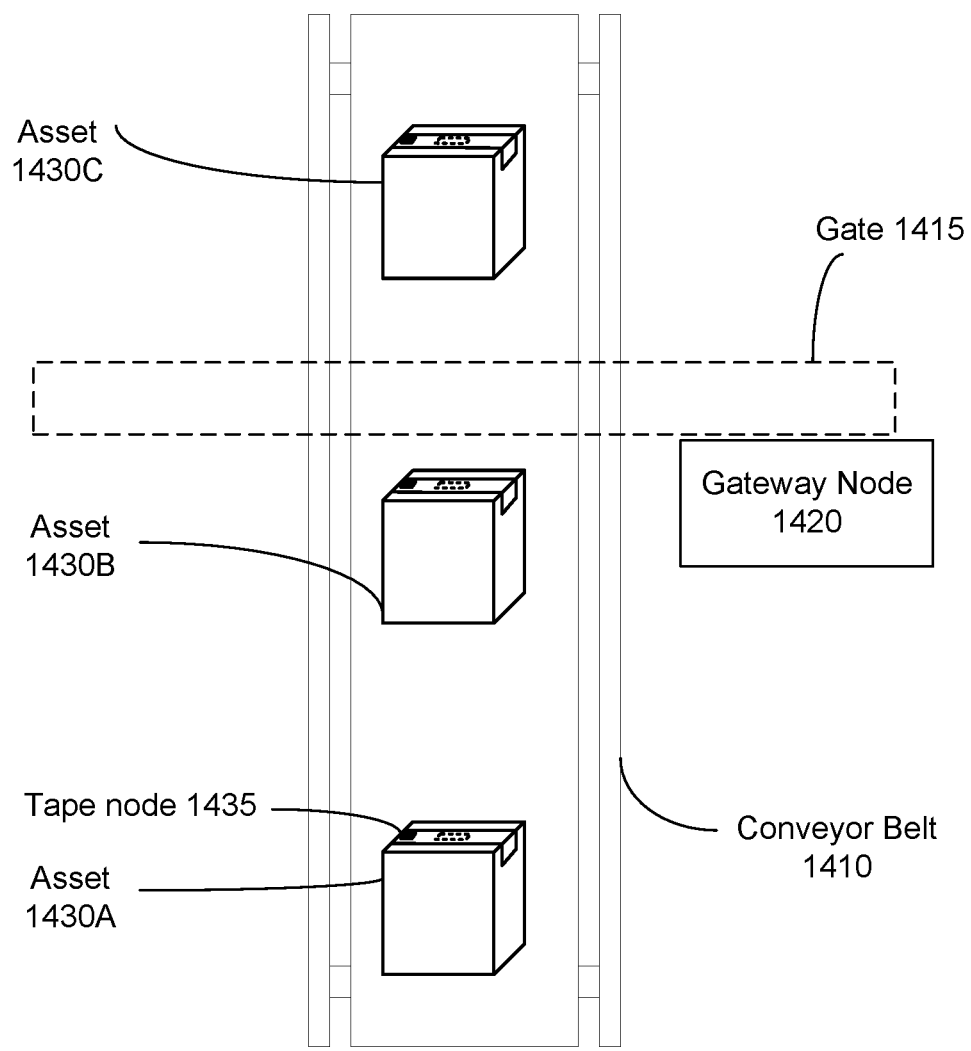
FIG. 14 shows a gateway node associated with a conveyor belt that communicates with one or more assets being transported on the conveyor belt, according to some embodiments.

FIG. 14 shows a gateway node 1420 associated with a conveyor belt 1410 that communicates with one or more assets 1430A-1430C (collectively referred to as the "assets 1430") being transported on the conveyor belt 1410, according to some embodiments. The assets 1430 transported by the conveyor belt 1410 pass through a gate 1415 which is an area of interest for the tracking system 400. One or more of the assets 1430 includes a tape node adhered to the asset for tracking the asset. For example, the asset 1430A includes a tape node 1435 that is attached to the asset 1430A. The gate may be an entranceway, an exit, a checkpoint, or some other are of interest for the assets 1430. For example, the gate 1415 may correspond to an entrance of a loading area where vehicles (such as airplanes, trucks, or other vehicles) are loaded with assets 1430. In certain situations it may be important for users of the tracking system 400 to accurately determine when the assets 1430 have passed through the gate.

The gateway node 1420 is positioned near the gate 1415 and the conveyor belt 1410 and configured to communicate with tape nodes on the assets 1430. The location of the gateway node 1420 is stored on the gateway node and also registered in a database of the IOT system 400. The gateway node may provide information to the tape nodes, such as location data for the gateway node 1410 and/or the tape nodes. For example, the gateway node 1420 may determine a location of the tape node 1430A based on received signal strength of wireless communication signals received from the tape node 1430A and based on the known location of the gateway node. In some embodiments, an identifier for the conveyor belt 1410 is stored on the gateway node 1420, and the gateway node 1420 is associated with the conveyor belt.

The gateway node 1420 may receive or store information relevant to the conveyor belt, such as a speed that the conveyor belt 1410 is operating at for transporting the assets 1430. In some embodiments, the gateway node 1420 is coupled to the conveyor belt 1410 can control aspects of the conveyor belt, such as a speed of the conveyor belt or an emergency shut off for the conveyor belt. In some embodiments, the gateway node 1420 determines a speed of assets 1430A traveling on the conveyor belt, based on the received signal strength of wireless communications from the tape node 1435. If the determined speed differs from the operation speed of the conveyor belt 1410 by an anomalous amount (e.g., the difference is greater than a threshold), the gateway node 1420 may determine that an anomalous event has occurred for the asset 1430 and take further actions, in response. For example, if the gateway node detects that the asset 1430A is not moving, the gateway node may determine that the asset 1430A has fallen off the conveyor belt 1410.

As the asset 1430A approaches the gate 1415, the gateway node instructs the tape node 1435 to increase functions related to tracking the asset 1430, such as increasing the amount or frequency of wireless communications performed by the tape node 1435. As discussed above, increased frequency of heartbeat signals (i.e., having the tape node 1435 check in to the IOT system 400 more frequently) of the tape node may increase the granularity and fidelity of tracking data for the asset 1430A. If the gate 1415 is a critical juncture of the journey for the asset 1430A, accurate tracking of the asset 1430A around the gate is valuable to the tracking system 400. Thus, in some embodiments, the gateway node 1420 enables increased tracking data collected by the tracking system 400 from the tape node 1435 around the gate 1415. In some further embodiments, the gateway node 1420 is positioned upstream on the conveyor belt 1410 from the gate 1415 and provides a schedule for wireless communication and location tracking functions to the tape node 1435 when the gateway node 1420 and the tape node 1435 wirelessly connect to each other. The schedule may be based on a speed of the conveyor belt 1410. For example, if the gateway node 1420 determines that the asset 1430A will reach the gateway in 10 minutes from a current time, the schedule may include having the tape node 1435 increase communication and tracking functions from the current time.

Computer Apparatus

Figure 15:
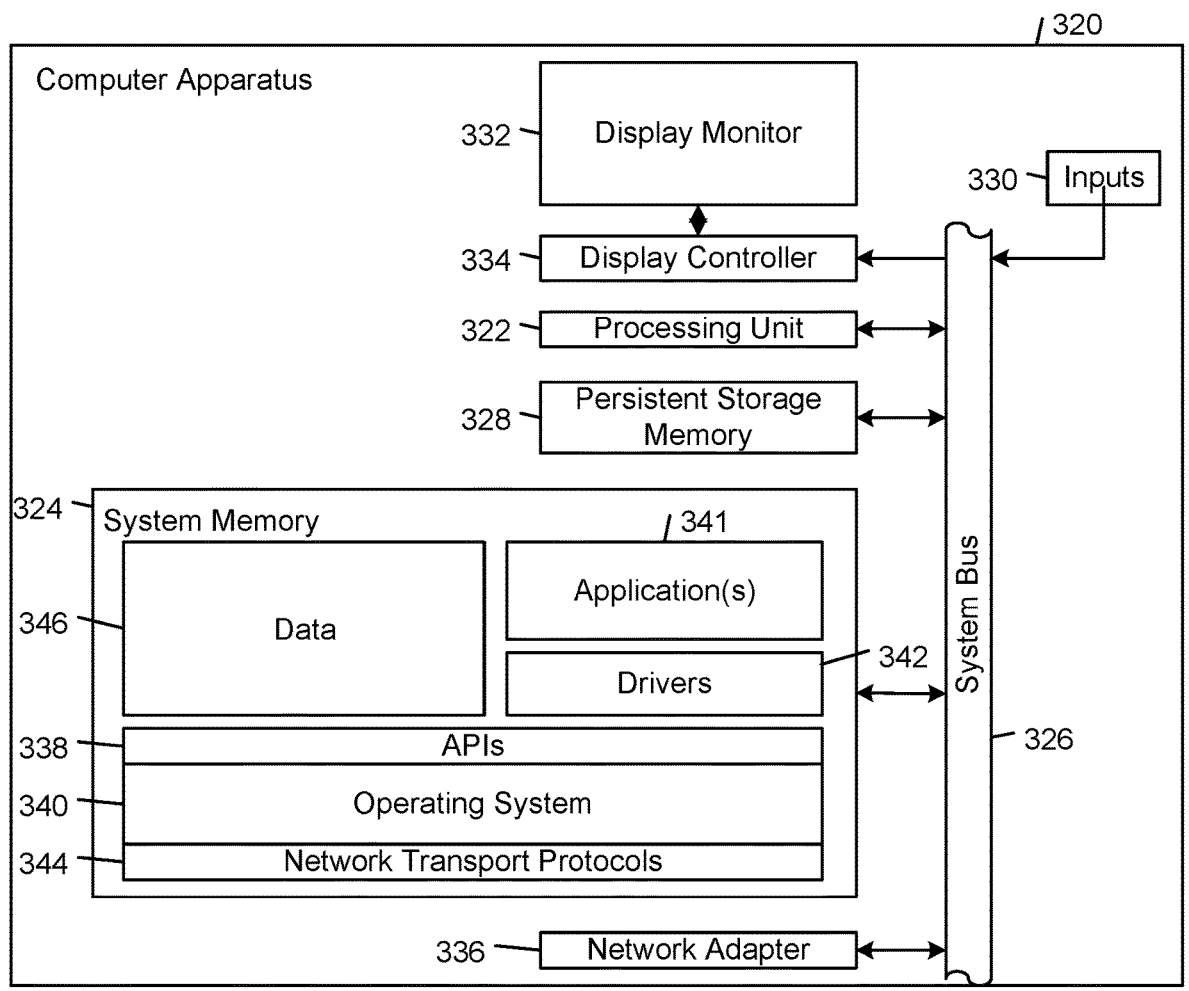
FIG. 15 shows an example embodiment of computer apparatus, according to some embodiments.

FIG. 15 shows an example embodiment of computer apparatus 320 that, either alone or in combination with one or more other computing apparatus, is operable to implement one or more of the computer systems described in this specification.

The computer apparatus 320 includes a processing unit 322, a system memory 324, and a system bus 326 that couples the processing unit 322 to the various components of the computer apparatus 320. The processing unit 322 may include one or more data processors, each of which may be in the form of any one of various commercially available computer processors. The system memory 324 includes one or more computer-readable media that typically are associated with a software application addressing space that defines the addresses that are available to software applications. The system memory 324 may include a read only memory (ROM) that stores a basic input/output system (BIOS) that contains start-up routines for the computer apparatus 320, and a random access memory (RAM). The system bus 326 may be a memory bus, a peripheral bus or a local bus, and may be compatible with any of a variety of bus protocols, including PCI, VESA, Microchannel, ISA, and EISA. The computer apparatus 320 also includes a persistent storage memory 328 (e.g., a hard drive, a floppy drive, a CD ROM drive, magnetic tape drives, flash memory devices, and digital video disks) that is connected to the system bus 326 and contains one or more computer-readable media disks that provide non-volatile or persistent storage for data, data structures and computer-executable instructions.

A user may interact (e.g., input commands or data) with the computer apparatus 320 using one or more input devices 330 (e.g. one or more keyboards, computer mice, microphones, cameras, joysticks, physical motion sensors, and touch pads). Information may be presented through a graphical user interface (GUI) that is presented to the user on a display monitor 332, which is controlled by a display controller 334. The computer apparatus 320 also may include other input/output hardware (e.g., peripheral output devices, such as speakers and a printer). The computer apparatus 320 connects to other network nodes through a network adapter 336 (also referred to as a "network interface card" or NIC).

A number of program modules may be stored in the system memory 324, including application programming interfaces 338 (APIs), an operating system (OS) 340 (e.g., the Windows® operating system available from Microsoft Corporation of Redmond, Wash. U.S.A.), software applications 341 including one or more software applications programming the computer apparatus 320 to perform one or more of the steps, tasks, operations, or processes of the locationing and/or tracking systems described herein, drivers 342 (e.g., a GUI driver), network transport protocols 344, and data 346 (e.g., input data, output data, program data, a registry, and configuration settings).

Examples of the subject matter described herein, including the disclosed systems, methods, processes, functional operations, and logic flows, can be implemented in data processing apparatus (e.g., computer hardware and digital electronic circuitry) operable to perform functions by operating on input and generating output. Examples of the subject matter described herein also can be tangibly embodied in software or firmware, as one or more sets of computer instructions encoded on one or more tangible non-transitory carrier media (e.g., a machine readable storage device, substrate, or sequential access memory device) for execution by data processing apparatus.

The details of specific implementations described herein may be specific to particular embodiments of particular inventions and should not be construed as limitations on the scope of any claimed invention. For example, features that are described in connection with separate embodiments may also be incorporated into a single embodiment, and features that are described in connection with a single embodiment may also be implemented in multiple separate embodiments. In addition, the disclosure of steps, tasks, operations, or processes being performed in a particular order does not necessarily require that those steps, tasks, operations, or processes be performed in the particular order; instead, in some cases, one or more of the disclosed steps, tasks, operations, and processes may be performed in a different order or in accordance with a multi-tasking schedule or in parallel.

Other embodiments are within the scope of the claims.

ADDITIONAL EMBODIMENTS

Additional Configuration Information

The foregoing description of the embodiments of the disclosure have been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A method comprising:
    receiving, by a first node of a wireless sensing system, a first communication and a second communication generated by a tape node associated with a mobile asset;
    receiving, by a second node of the wireless sensing system, the first communication and the second communication generated by the tape node associated with the mobile asset;
    computing, by the wireless sensing system, a direction of movement of the tape node associated with the mobile asset, the direction of movement based at least in part on respective signal strengths of the first communication and the second communication as received by the first node and the second node;
    computing, by the wireless sensing system, a speed of the tape node associated with the mobile asset; and
    transmitting a schedule to the tape node based on the speed, the schedule defining a future time to alter communication function of the tape node.

2. The method of claim 1, further comprising:
    based on the direction of movement, determining, by the wireless sensing system, a most likely path of the tape node; and
    based on the most likely path of the tape node, transmitting a configuration instruction to the tape node.

3. The method of claim 1, wherein the schedule further includes a configuration instruction, the configuration instruction comprising one or more of: an instruction to increase or decrease a frequency of communication; an instruction to communicate via a different or additional channel; an instruction to cease communication with one or more nodes; an instruction to initiate communication with one or more nodes.

4. The method of claim 2, wherein a determined most likely path of the tape node includes a destination, and wherein the configuration instruction is based at least in part on the destination.

5. The method of claim 1, wherein the first node and the second node are deployed at locations based on a structural threshold of a building.

6. The method of claim 1, wherein computing a direction of movement of the tape node further comprises applying a machine learned model, the machine learned model trained to receive one or more measures of signal strengths as input and to output a most likely direction of movement.

7. The method of claim 1, further comprising transmitting, by a leading indicator of the wireless sensing system, an instruction to the tape node associated with the mobile asset, wherein the instruction comprises one or more of: an instruction to increase or decrease a frequency of communication; an instruction to communicate via a different or additional channel; an instruction to cease communication with one or more nodes; an instruction to initiate communication with one or more nodes.

8. The method of claim 7, wherein the leading indicator of the wireless sensing system is a gateway node of a wireless sensing system and the instruction is transmitted responsive to the leading indicator detecting that the tape node is within a threshold distance of a location.

9. The method of claim 1, further comprising: based on the likely path of the tape node and based on a known location of the first node and a known location of the second node, determining whether the tape node will travel through or near an area of interest.

10. The method of claim 9, wherein the area of interest corresponds to a gate, an entrance, an exit, or a checkpoint.

11. The method of claim 9, further comprising:
    based on the direction of movement, determining, by the wireless sensing system, a most likely path of the tape node;
    based on the most likely path of the tape node, transmitting a configuration instruction to the tape node to increase a frequency of communication, and
    updating a determined location of the tape node with higher frequency or granularity than before the configuration instruction was transmitted, based on the tape node increasing the frequency of communication.

12. The method of claim 1, wherein the first node and the second node are associated with a conveyor belt, and the mobile asset is being transported by the conveyor belt.

13. The method of claim 1, wherein the mobile asset is on a vehicle, the first node is a gateway node associated with the vehicle, and the second node is a gateway node associated with a destination of the vehicle.

14. A tracking system comprising:
    a first gateway node in a known first location configured to wirelessly communicate with a tape node;
    a second gateway node in a known second location configured to wirelessly communicate with the tape node; and
    the tape node associated with a mobile asset and configured to wirelessly communicate with the first gateway node and the second gateway node,
    wherein:
        the tracking system determines a direction of movement of the tape node associated with the mobile asset, the direction of movement determined based at least in part on wireless communications between the tape node and the first gateway node, wireless communications between the tape node and the second gateway node, the known first location, and the known second location;
        the tracking system determines a speed of the tape node; and
        the tape node is provided a schedule based on the speed, the schedule defining a future time to alter communication function of the tape node.

15. The tracking system of claim 14, wherein, based on the determined direction of movement, tracking system determines a most likely path of the tape node.

16. The tracking system of claim 15, wherein the tracking system determines if the tape node will travel through or near an area of interest based on the determined most likely path.

17. The tracking system of claim 14, wherein the first known location and the second known location are in a proximity of a gate, doorway, entrance, exit, or a checkpoint.

18. The tracking system of claim 14, wherein the first known location and the second known location are in a same environment.

19. The tracking system of claim 14, wherein the first gateway node is associated with a conveyor belt transporting the mobile asset.

20. The tracking system of claim 19, wherein the first gateway node stores or receives information on the conveyor belt including an operational speed of the conveyor belt, and the speed of the tape node is determined using the operational speed of the conveyor belt.

\* \* \* \* \*